US007115710B2

(12) United States Patent
Plowman et al.

(10) Patent No.: US 7,115,710 B2
(45) Date of Patent: Oct. 3, 2006

(54) DIAGNOSIS AND TREATMENT OF PTP RELATED DISORDERS

(75) Inventors: Gregory D. Plowman, San Carlos, CA (US); Bahija Jallal, Menlo Park, CA (US)

(73) Assignee: Sugen, Inc., South San Francisco, CA (US)

( * ) Notice: Subject to any disclaimer, the term of this patent is extended or adjusted under 35 U.S.C. 154(b) by 289 days.

(21) Appl. No.: 09/095,478

(22) Filed: Jun. 10, 1998

(65) Prior Publication Data

US 2003/0095970 A1 May 22, 2003

Related U.S. Application Data

(60) Provisional application No. 60/049,756, filed on Jun. 11, 1997.

(51) Int. Cl.
*C07K 14/00* (2006.01)
*C07K 14/435* (2006.01)

(52) U.S. Cl. .................... 530/350; 530/828; 530/829

(58) Field of Classification Search ............ 530/300, 530/350, 828, 829; 435/183, 320.1, 69.1, 435/325, 252.3, 254.11, 254.2, 410, 348; 536/23.5, 23.4

See application file for complete search history.

(56) References Cited

U.S. PATENT DOCUMENTS

| | | | |
|---|---|---|---|
| 4,343,940 A | 8/1982 | Kreighbaum et al. | 544/283 |
| 4,376,110 A | 3/1983 | David et al. | 436/513 |
| 4,447,608 A | 5/1984 | Jones et al. | 544/287 |
| 4,757,072 A | 7/1988 | Kabbe et al. | 514/257 |
| 4,945,050 A | 7/1990 | Sanford et al. | 435/172.1 |
| 5,217,999 A | 6/1993 | Levitzki et al. | 514/613 |
| 5,283,173 A | 2/1994 | Fields et al. | 435/6 |
| 5,302,606 A | 4/1994 | Spada et al. | 514/357 |
| 5,316,553 A | 5/1994 | Kaul et al. | 8/639 |
| 5,330,992 A | 7/1994 | Eissenstat et al. | 814/312 |
| 5,602,171 A | 2/1997 | Tang et al. | 514/455 |
| 5,610,173 A | 3/1997 | Schwartz et al. | 514/378 |

FOREIGN PATENT DOCUMENTS

| | | |
|---|---|---|
| EP | 0 520 722 A1 | 12/1992 |
| EP | 0 562 734 A1 | 9/1993 |
| EP | 0 566 226 A1 | 10/1993 |
| WO | 91/15495 | 10/1991 |
| WO | 92/20642 | 11/1992 |
| WO | 92/21660 | 12/1992 |
| WO | 93/09236 | 5/1993 |
| WO | 94/03427 | 2/1994 |
| WO | 94/14808 | 7/1994 |
| WO | 94/23039 | 10/1994 |
| WO | 96/22976 | 8/1996 |

OTHER PUBLICATIONS

Patel et al, Journal of Biological Chemistry, 1999, vol. 274, pp. 7958–7968, abstract.*
Kume et al, Journal of Biological Chemistry, 1996, vol. 271, pp. 30916–30921, abstract.*
Li et al, Cell Signaling, 1996, vol. 8, pp. 467–473, abstract.*
Xie et al, Cancer Research, 1996, vol. 56, pp. 2742=2744, abstract.*
Partanen, Anticancer Research, 1996, vol. 16, pp. 943–946, abstract.*
Tabiti et al, Cancer Letters, 1995, vol. 93, pp. 239–248, abstract.*
Maekawa et al, FEBS Letters, 1994, vol. 337, pp. 200–206, abstract.*
Jones et al (Journal of Biological Chemistry, 1989, vol. 264, pp. 7747–7753).*
Ahmad et al (Journal of Clinical Investigation, 1995, vol. 85, pp. 2806–2812).*
Norris et al (FEBS Letters, 1997, vol. 415, pp. 243–248).*
Abe et al., "Molecular Characterization of a Novel Metabotropic Glutamate Receptor mGluR5 Coupled to Inositol Pohosphate/$Ca^{2+}$Signal," *J. Biol. Chem.* 267(19):13361–13368 (1992).
Allen et al., "Modulation of CD4 by suramin," *Clin. Exp. Immunol.* 91:141–146 (1991).
Altschul et al., "Basic Local Alignment Search Tool," *J. Mol. Biol.* 215:403–410 (1990).
Anafi et al., "Tyrphostin–Induced Inhibition of $p210^{bcr-abl}$ Tyrosine Kinase Activity Induces K562 to Differentiate," *Blood* 82:3524–3529 (1993).
Baker et al., "Induction of acetylcholine receptor clustering by native polystyrene beads," *Journal of Cell Science* 102:543–555 (1992).
Barker et al., "*In vitro* activity of non–glutamate containing quinazoline–based thymidylate synthase inhibitors," *Proceedings of the American Association for Cancer Research* 32:327 at abstract No. 1939 (1991).
Bayer et al., "The Avidin–Biotin Complex in Affinity Cytochemistry," *Methods in Enzymology* 62:308–319 (1979).
Benoist and Chambon, "*In vivo* sequence requirements of the SV40 early promoter region," *Nature* 290:304–310 (1981).

(Continued)

*Primary Examiner*—Karen A. Canella
(74) *Attorney, Agent, or Firm*—Beth A. Burrous; Gregg C. Benson; Nicholas I. Slepchuk, Jr.

(57) ABSTRACT

The present invention relates to PTP05 polypeptides and PTP10 polypeptides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for PTP05 and/or PTP10 related diseases or conditions characterized by an abnormal interaction between a PTP05 polypeptide and a PTP05 binding partner and/or a PTP10 polypeptide and a PTP10 binding partner.

5 Claims, 2 Drawing Sheets

OTHER PUBLICATIONS

Bertino, "Toward Improved Selectivity in Cancer Chemotherapy: The Richard and Hinda Rosenthal Foundation Award Lecture," *Cancer Research* 39:293–304 (1979).

Bilder et al., "Tyrphostins inhibit PDGF–induced DNA synthesis and associated early events in smooth muscle cells," *Am. J. Physiol.* 260(Cell Physiol.29):C721–C730 (1991).

Bollon and Stauver, "DNA Transformation Efficiency of Various Bacterial and Yeast Host–Vector Systems," *Journal of Clinical Hematology and Oncology* 10(2&3):39–48 (1980).

Botstein et al., "Making Mutations in vitro and Putting Them Back into Yeast," *Miami Winter Symposia—From Gene to Protein: Translation into Biotechnology*, edited by Ahma et al., Academic Press, 19:265–274 (1982).

Brinster et al., "Factors Affecting the Efficiency of Introducing Foreign DNA into Mice by Microinjecting Eggs," *Proc. Natl. Acad. Sci. USA* 82:4438–4442 (1985).

Broach, "The Yeast Plasmid 2μ Circle," *Cell* 28:203–204 (1982).

Broach, "The Yeast Plasmid 2μ Circle," in *The Molecular Biology of the Yeast Saccharomyces: Life Cycle and Inheritance*, Cold Spring Harbor Laboratory, Cold Spring Harbor, NY, pp. 445–470 (1981).

Brunton et al., "Anti–tumour activity of novel tryphostins in breast cancer cells," *Proceedings of the American Association for Cancer Research* 33:558 at abstract No. 3335 (1992).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bullock et al., "Techniques in Immunocytochemistry," Academic Press, Orlando, FL: vol. 1 (1982), vol. 2 (1983), vol. 3 (1985) (Table of Contents Only).

Burke et al., "Arylamides of Hydroxylated Isoquinolines as Protein–Tyrosine Kinase Inhibitors," *Bioorganic & Medical Chemistry Letters* 2(12):1771–1774 (1992).

Burke et al., "Bicyclic Compounds as Ring–Constrained Inhibitors of Protein–Tyrosine Kinase $p56^{ick\ 1}$," *Journal of Medicinal Chemistry* 36(4):425–432 (1993).

Campbell, *Monoclonal Antibody Technology: Laboratory Techniques in Biochemistry and Molecular Biology*, vol. 13, Elsevier Science Publishers, Amsterdam, The Netherlands (1984) (Table of Contents Only).

Capecchi, "Altering the Genome by Homologous Recombination," *Science* 244:1288–1292 (1989).

Capecchi, "High Efficiency Transformation by Direct Microinjection of DNA into Cultured Mammalian Cells," *Cell* 22:479–488 (1980).

Cenatiempo, "Prokaryotic gene expression in vitro: transcription–translation coupled systems," *Biochimie* 68:505–515 (1986).

Chard, *An–Introduction to Radioimmunoassay and Related Techniques*, Elsevier Science Publishers, Amsterdam, The Netherlands (1986) (Table of Contents Only).

Chater et al., "Streptomyces ØC31–Like Phages: Cloning Vectors, Genome Changes and Host Range," in *Sixth International Symposium on Actinomycetes Biology*, edited by Szabe et al., Akademiai Kaido, Budapest, Hungary, pp. 45–52 (1986).

Chen and Okayama, "High–Efficiency Transformation of Mammalian Cells by Plasmid DNA," *Molecular and Cellular Biology* 7(8):2745–2752 (1987).

Chomczynski and Sacchi, "Single–Step Method of RNA Isolation by Acid Guanidinium Thiocyanate–Phenol–Chloroform Extraction," *Analytical Biochemistry* 162:156–159 (1987).

Chu et al., "Electroporation for the efficient transfection of mammalian cells with DNA," *Nucleic Acids Research* 15:1311–1326 (1987).

Curiel et al., "Gene Transfer to Respiratory Epithelial Cells via the Receptor–mediated Endocytosis Pathway," *Am. J. Respir. Cell. Mol. Biol.* 6:247–252 (1992).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Dolle et al., "5,7–Dimethoxy–3–(4–pyridinyl)quinoline is a Potent and Selective Inhibitor of Human Vascular—Type Platelet–Derived Growth Factor Receptor TyrosineKinase," *J. Med. Chem.* 37:2627–2629 (1994).

Dong et al., "Activation of tumoricidal properties in macrophages by lipopolysaccharide requires protein–tyrosine kinase activity," *Journal of Leukocyte Biology* 53:53–60 (1993).

Dong et al., "Protein Tyrosine Kinase Inhibitors Decrease Induction of Nitric Oxide Synthase Activity in Lipopolysaccharide–Responsive and Lipopolysaccharide–Nonresponsive Murine Macrophages," *The Journal of Immunology* 151(5):2717–2724 (1993).

Dreborg et al., "Ch. 10—The chemistry and standardization of allergens," in *Handbook of Experimental Immunology–vol. 1: Immunochemistry*, 4th Ed., edited by Weir et al., Blackwell Scientific Publications, Oxford, England, pp. 10.1–10.28 (1986).

Engvall and Perlmann, "Enzyme–Linked Immunosorbent Assay, ELISA. III. Quantitation of Specific Antibodies by Enzyme–Labeled Anti–Immunoglobulin in Antigen–Coated Tubes," *J. Immunology*, 109:129–135 (1972) (mistakenly referred to as Engval).

Felgner and Ringold, "Cationic liposome–mediated transfection," *Nature* 337–388 (1989).

Felgner et al., "Lipofection: A Highly Efficient, Lipid–mediated DNA–transfection Procedure," *Proc. Natl. Acad. Sci. USA* 84:7413–7417 (1987).

Fernandes et al., "Biochemical and Antitumor Effects of 5,8–Dideazaisopteroylglutamate, a Unique Quinazoline Inhibitor of Thymidylate Synthase," *Cancer Research* 43:1117–1123 (1983).

Ferris et al., "Synthesis of Quinazoline Nucleosides from Ribose and Anthranilonitrile. Application of Phase–Transfer Catalysis in Nucleoside Synthesis," *J. Org. Chem*, 44(2):173–178 (1979).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Fry et al., "A Specific Inhibitor of the Epidermal Growth Factor Receptor Tyrosine Kinase," *Science* 265:1093–1095 (1994).

Gazit et al., "Tyrphostins 1. Synthesis and Biological Activity of Protein Tyrosine Kinase Inhibitors," *J. Med. Chem.* 32:2344–2352 (1989).

Gazit et al., "Tyrphostins. 3. Structure–Activity Relationship Studies of a –Substitued Benzylidenemalononitrile 5–S–Aryltyrphostins," *J. Med. Chem.* 36:3556–3564 (1993).

Gennaro (editor), *Remington's Pharmaceutical Sciences* (1990) (Table of Contents Only).

Gerard et al., "cDNA synthesis by cloned moloney murine leukemia virus reverse transcriptase lacking Rnase H Activity," Focus 11:66–69 (1989).

Gilman et al., "Isolation of sigma–28–specific promoters from *Bacillus subtilis* DNA," *Gene* 32:11–20 (1984)

Gishizky et al., "Mutant forms of growth factor–binding protein–2 reversce BCR–ABL–induced transformation," *Proc. Natl. Acad. Sci. USA* 92:10889–10893 (1995).

Glick and Whitney, "Factors affecting the expression of foreign proteins in *Escherichia coli,*" *Journal of Industrial Microbiology* 1:277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol*, 35:365–403 (1981).

Gottesman, "Bacterial Regulation: Global Regulatory Networks," *Ann. Rev. Genet.* 18:415–441 (1984).

Gryczan, "Ch. 10—Molecular Cloning in *Bacillus subtilis*," in *The Molecular Biology of the Bacilli*, edited by Dubnau, Academic Press, New York, pp. 307–329 (1982).

Hamer and Walling, "Regulation *In Vivo* of a Cloned Mammalian Gene: Cadmium Induces the Transcription of a Mouse Metallothionein Gene in SV40 Vectors," *J. of Molecular and Applied Genetics* 1:273–288 (1982).

Hammer et al., "Spontaneous Inflammatory Disease in Transgenic Rats Expressing HLA–B27 and Human, $_2$m: An Animal Model of HLA–B27–Associated Human Disorders," *Cell* 63:1099–1112 (1990).

Hanks and Hunter, "The eukaryotic protein kinase superfamily: kinase (catalytic) domain structure and classfication," *FASEB J*, 9:576–596 (1995).

Haslam et al., "Pleckstrin domain homology," *Nature* 363:309–310 (1993).

Houdebine and Chourrout, "Transgenesis in Fish," *Experientia* 47:891–897 (1991).

Hurby et al., in *Synthetic Peptides: A User's Guide*, edited by Grant, Washington University School of Medicine, W.H. Freeman and Company, New York, pp. 289–307 (1992).

Innis et al., *PCR Protocols: A Guide to Methods and Applications*, edited by Michael A. Innis et al., Academic Press, San Diego (1990) (Table of Contents Only).

Izaki, *Japanese Journal of Bacteriology* 33(6):729–742 (1978) (In Japanese).

Jackman, "ICI D1694, a Quinazoline Antifolate Thymidylate Synthase Inhibitor That Is a Potent Inhibitor of L1210 Tumor Cell Growth *in Vitro* and *in Vivo* : A New Agent for Clinical Study," *Cancer Research* 51:5579–5586 (1991).

Jasny, "Insect Viruses Invade Biotechnology," *Science* 238:1653 (1987).

John and Twitty, "Plasmids as Epidemiologic Markers in Nosocomial Gram–Negative Bacilli: Experience at a University and Review of the Literature," *Reviews of Infectious Diseases* 8:693–704 (1986).

Johnston and Hopper, "Isolation of the yeast regulatory gene *GAL4* and analysis of its dosage effects on the galactose/melibiose regulon," *Proc. Natl. Acad. Sci. USA* 79:6971–6975 (1982).

Jones et al., "Quinazoline Antifolates Inhibiting Thymidylate Synthase: Varation of the Amino Acid," *J. Med. Chem*, 29:1114–1118 (1986).

Joyner et al., "Production of a mutation in mouse *En–2* gene by homologous recombination in embryonic stem cells," *Nature* 338:153–156 (1989).

Kasprzak et al., "Location of a Contact Site Between Actin and Myosin in the Three–Dimensional Structure of the Acto–S1 Complex," *Biochemistry* 28:9230–9238 (1989).

Kaur, "Tyrphostin induced growth inhibition: correlation with effect on p210$^{bcr-abl}$ autokinase activity in K562 chronic myelogenous leukemia," *Anti–Cancer Drugs* 5:213–222 (1994).

Kendall and Cohen, "Plasmid Transfer in *Streptomyces Iividans*: Identification of a *kil–kor* System Associated with the Transfer Region of PIJ101," *Journal of Bacteriology* 169:4177–4183 (1987).

King et al., "Site–specific dephosphorylation and deactivation of the human insulin receptor tyrosine kinase by particulate and soluble phosphotyrosyl protein phosphatases," *Biochem. J.* 275:413–418 (1991).

Köhler and Milstein, "Continuous cultures of fused cells secreting antibody of predefined specificity," *Nature* 256:495–497 (1975).

Krueger and Saito, "A human transmembrane protein–tyrosine–phosphatase, PTP. , is expressed in brain and has an N–terminal receptor domain homologous to carbonic anhydrases," *Proc. Natl. Acad. Sci. USA* 89:7417–7421 (1992).

Kuo et al., "Effects of signalling transduction modulators on the transformed phenotypes in *v*–H–*ras*–transformed NIH 3T3 cells," *Cancer Letters* 74:197–202 (1993).

Lee and Skibo, "Active–Site–Directed Reductive Alkylation of Xanthine Oxidase by Imidazo[4,5–*g*]quinazoline–4,9–diones Functionalized with a Leaving Group," *Biochemistry* 26:7355–7362 (1987).

Lemus et al., "Studies of Extended Quinone Methides. Synthesis and Physical Studies of Purine–like Monofunctional and Bifunctional Imidazo[4,5–*g*]quinazoline Reductive Alkylating Agents," *J. Org. Chem*, 54:3611–3618 (1989).

Levitzki, "Tyrphostins: tyrosine kinase blockers as novel antiproliferative agents and dissectors of signal transduction," *FASEB J.*, 6:3275–3282 (1992).

Ley and Seng, "Synthesis Using Benzofuroxan," *Synthesis* 1975:415–422 (1975) (in German).

Lutz et al., "The Distribution of Two hnRNP–Associated Proteins Defined by a Monoclonal Antibody Is Altered in Heat–Shocked HeLa Cells," *Experimental Cell Research* 175:109–124 (1988).

Lyall et al., "Tyrphostins Inhibit Epidermal Growth Factor (EGF)–Receptor Tyrosine Kinase Activity in Living Cells and EGF–stimulated Cell Proliferation," *J. Biol. Chem.* 264:14503–14509 (1989).

Maniatis, "Ch. 11—Recombinant DNA Procedures in the Study of Eukaryotic Genes," in *Cell Biology: A Comprehensive Treatise, vol. 3, Gene Sequence Expression*, Academic Press, NY, pp. 563–608 (1980).

Maxwell et al., "$^{19}$F Nuclear Magnetic Resonance Imaging of Drug Distribution *in Vivo*: The Diposition of an Antifolate Anticancer Drug in Mice," *Magnetic Resonance in Medicine* 17:189–196 (1991).

Mayer and Baltimore, "Signalling through SH2 and SH3 domains," *Trends in Cell Biology* 3:8–13 (1993).

Mayer et al., "A novel viral oncogene with structural similarity to phospholipase C," *Nature* 332:272–275 (1988).

McKnight, "Functional Relationships between Transcriptional Control Signals of the Thymidine Kinase Gene of Herpes Simplex Virus," *Cell* 31:355–365 (1982).

Miller and Rosman, "Improved Retroviral Vectors for Gene Transfer and Expression," *BioTechniques* 7(9):982–990 (1989).

Miller et al., "An Insect Baculovirus Host–Vector System for High–Level Expression of Foreign Genes," in *Genetic Engineering: Principles and Methods*, edited by Setlow et al., Plenum Press, 8:277–298 (1986).

Miller, "Human gene therapy comes of age," *Nature* 357:455–460 (1992).

Mini et al., "Cytotoxic Effects of Folate Antagonists against Methotrexate–resistant Human Leukemic Lymphoblast CCRF–CEM Cell Lines," *Cancer Research* 45:325–330 (1985).

Mulligan, "The Basic Science of Gene Therapy," *Science* 260:926–932 (1993).

Nelson, "Detection of Acridinlum Esters by Chemiluminescence," *Nonisotopic DNA Probe Techniques*, ed. Larry J. Kricka, (San Diego: Academic Press, Inc.) pp. 275–310 (1992).

Okayama and Berg, "A cDNA Cloning Vector That Permits Expression of cDNA Inserts in Mammalian Cells," *Molecular and Cellular Biology* 3:280–289 (1983).

Pawson and Schlessinger, "SH2 and SH3 domains," *Current Biology* 3(7):434–442 (1993).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Phillips and Castle, "Quino[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Piliemer et al., "Insulin Dependence of Murine Lymphoid T–Cell Leukemia," *Brit. J. Cancer* 50:80–85 (1992).

Ponting and Bork, "Pleckstrin's repeat performance: a novel domain in G–protein signaling?" *TIBS* 21:245–246 (1996).

Posner et al., Kinetics of Inhibition by Tyrphostins of the Tyrosine Kinase Activity of the Epidermal Growth Factor Receptor and Analysis by a New Computer Program, *Molecular Pharmacology* 45:673–683 (1993).

Pursel et al., "Genetic Engineering of Livestock," *Science* 244:1281–1288 (1989).

Redemann et al., "Anti–Oncogenic Activity of Signalling–Defective Epidermal Growth Factor Receptor Mutants," *Molecular and Cellular Biology* 12(2):491–498 (1992).

Reece et al., "Pharmacokinetics of Trimetrexate Administered by Five–Day Continuous Infusion to Patients with Advanced Cancer," *Cancer Research* 47:2996–2999 (1987).

Rendu et al., "Inhibition of Platelet Activation by Tyrosine Kinase Inhibitors," *Biochemical Pharmacology* 44(5):881–888 (1992).

Robertson, *Teratocarcinomas and embryonic stem cells: a practical approach*, IRL Press (1987) (Table of Contents).

Rubin, "*Drosophila melanogaster* as an Experimental Organism," *Science* 240:1453–1459 (1988).

Sadowski et al., A Noncatalytic Domain Conserved among Cytoplasmic Protein–Tyrosine Kinases Modifies the Kinase Function and Transforming Activity of Fujinami Sarcoma Virus $P130^{gag-fps}$, *Molecular and Cellular Biology* 6(12):4396–4408 (1986).

Saito and Streuli, "Molecular Characterization of Protein Tyrosine Phosphatases," *Cell Growth & Differentiation* 2:59–65 (1991).

Sambrook and Maniatis., *Molecular Cloning: A Laboratory Manual, 2$^{nd}$ Edition*, Cold Spring Harbor Laboratory Press (1989) (Table of Contents).

Sauro and Thomas, "Decreased Sensitivity of Aorta from Hypertensive Rats to Vasorelaxation by Tyrphostin," *Life Sciences* 53:PL371–376 (1993).

Sauro and Thomas, "Tyrphostin Attenuates Platelet–Derived Growth Factor–Induced Contraction in Aortic Smooth Muscle Through Inhibition of Protein Tyrosine Kinase(s)," *The Journal of Pharamacology and Experimental Therapeutics* 267:1119–1125 (1993).

Sclier et al., "Role of an Intensive Care Unit (ICU) in a Medical Onocology Department," *Cancer Immunol, and Immunotherapy* 23:A65 at abstract No. 257 (1986).

Sikora and Grzelakowska–Sztabert, "Quinazoline CB 3717 and CB 3703 Inhibitors of Folate Retention and Metabolism in Ehrlich Ascites Carcinoma Cells and Some Organs of the Host–Mouse," *Cancer Letters* 23:289–295 (1984).

Sikora et al., "Development of an Assay for the Estimation of $N^{10}$–Propargyl–5,8–dideazafolic Acid Polyglutamates in Tumor Cells," *Analytical Biochemistry* 172:344–355 (1988).

Silver et al., "Amino terminus of the yeast *GAL4* gene product is sufficient for nuclear localization," *Proc. Natl. Acad. Sci. USA* 81:5951–5955 (1984).

Simons et al., "Gene Transfer into Sheep," *Bio/Technology* 6:179–182 (1988).

Smith and Johnson, "Single–step purification of polypeptides expressed in *Escherichia coli* as fusions with glutathione S–transferase," *Gene* 67:31–40 (1988).

St. Groth and Scheidegger, "Production of Monoclonal Antibodies: Strategy and Tactics," *J. Immunol. Methods* 35:1–21 (1980).

Stemberger et al., "The Unlabeled Antibody Enzyme Method of Immunohistochemistry: Preparation and Properties of Soluble Antigen–Antibody Complex (Horseradish Peroxidase–Antihorseradish Peroxidase) and its Use in Identification of Spirochetes," *J. Histochemistry and Cytochemistry* 18(5):315–333 (1970).

Superti–Furga et al., "Csk Inhibition of c–Src activity requires both the SH2 and SH3 domains of Src," *EMBO J.* 12:2625–2634 (1993).

Tijssen, *Practice and Theory of Enzyme Immunoassays: Laboratory Techniques in Biochemistry and Molecular Biology*, vol. 15, Elsevier Science Publishers, Amsterdam, The Netherlands (1985) (Table of Contents Only).

Ulmanen et al., "Transcription and Translation of Foreign Genes in *Bacillus subtilis* by the Aid of a Secretion Vector," *Journal of Bacteriology* 162:176–182 (1985).

Ward et al., "Construction and characterisation of a series of multi–copy promoter–probe plasmid vectors for *Streptomyces* using the aminoglycoside phosphotransferase gene from Tn5 as indicator," *Mol. Gen. Genet*, 203:468–478 (1986).

Wilchek and Jakoby, "The Literature on Affinity Chromatography," *Methods in Enzymology* 34:3–10 (1974) (also referred to as Jacoby).

Wolbring et al., "Inhibition of GTP–utilizing Enzymes by Tyrphostins," *J. Biol. Chem.* 269:22470–22472 (1994).

Yang et al., "*In Vivo* and *In Vitro* Gene Transfer to Mammalian Somatic Cells by Particle Bombardment," *Proc. Natl. Acad. Sci. USA* 87:9568–9572 (1990).

Yoneda et al., "The Antiproliferative Effects of Tyrosine Kinase Inhibitors Tyrphostins on a Human Squamous Cell Carcinoma *in Vitro* and Nude Mice," *Cancer Research* 51:4430–4435 (1991).

* cited by examiner

FIG. 1A

Identities = 295/320 (92%), positives = 295/320 (92), Strand = Plus/Plus

```
SuPTP10_r     1 GAAAATAATTGTAATGTTATTGCTATGATAACCAGAGAGATAGAAGGTGGAGTTATCAAG 60
                ||||||||||||||||||||||||||||||||||||||||||||| ||||||||||||||
SuPTP05_m  1060 GAAAATAATTGTAATGTTATTGCTATGATAACCAGAGAGATAGAATGTGGAGTTATCAAG 1119

SuPTP10_r    61 TGTTGCAGTTACTGGCCCGTTTCTCTGAAGGAGCCTTTGGAATTCAAACACTTTCATGTC 120
                |||| |||||||||||||| ||||||||||||||||||||||||| |||||||| ||||
SuPTP05_m  1120 TGTTACAGTTACTGGCCCATTTCTCTGAAGGAGCCTTTGGAATTCGAACACTTTAGTGTC 1179

SuPTP10_r   121 CTTCTGGAGAACTTTCAGATAACTCAGTATTTTGTCATCCGAATATTTCAAATTGTGAAG 180
                ||||||||| |||||| |||||||| |||||  | | ||| |||||| |||||||||||
SuPTP05_m  1180 TTTCTGGAGACCTTTCATGTAACTCAATATTTCACCGTTCGAGTATTTCAGATTGTGAAG 1239

SuPTP10_r   181 AAGTCCACAGGAAAGAGTCACTCTGTAAAACACTTGCAGTTCATCAAATGGCCAGACCAT 240
                ||||||||||||||||| || | ||||||||||||||||||||| ||| |||||||||||
SuPTP05_m  1240 AAGTCCACAGGAAAGAGCCAATGTGTAAAACACTTGCAGTTCACCAAGTGGCCAGACCAT 1299

SuPTP10_r   241 GGCACTCCTGCCTCAGTAGATTTTTTCATCAAATATGTCCGTTATGTGAGGAAGAGCCAC 300
                |||||||||||||||| ||||||||||||| ||||||||||||||||||||||||||||
SuPTP05_m  1300 GGCACTCCTGCCTCAGCAGATTTTTTCATAAAATATGTCCGTTATGTGAGGAAGAGCCAC 1359

SuPTP10_r   301 ATTACAGGACCCCTCCTTGT 320
                ||||||||||||||||||||
SuPTP05_m  1360 ATTACAGGACCCCTCCTTGT 1379
```

FIG. 1B

Identities = 91/107 (85%), Positives = 96/107 (89%), Frame = +1

```
SuPTP10_r    1 ENNCNVIAMITREIEGGVIKCCSYWPVSLKEPLEFKHFHVLLENFQITQYFVIRIFQIVK 180
               ENNCNVIAMITREIE GVIKC SYWP+SLKEPLEF+HF V LE F +TQYF +R+FQIVK
SuPTP05_m  251 ENNCNVIAMITREIECGVIKCYSYWPISLKEPLEFEHFSVFLETFHVTQYFTVRVFQIVK 310

SuPTP10_r  181 KSTGKSHSVKHLQFIKWPDHGTPASVDFFIKYVRYVRKSHITGPLLV 321
               KSTGKS VKHLQF KWPDHGTPAS DFFIKYVRYVRKSHITGPLLV
SuPTP05_m  311 KSTGKSQCVKHLQFTKWPDHGTPASADFFIKYVRYVRKSHITGPLLV 357
```

DIAGNOSIS AND TREATMENT OF PTP RELATED DISORDERS

RELATED APPLICATIONS

This application claims priority to the U.S Provisional Patent Application No. 60/049,756, by Plowman et al., entitled "Diagnosis and Treatment of PTP Related Disorders," and filed Jun. 11, 1997, which is incorporated herein by reference in its entirety, including any drawings.

FIELD OF THE INVENTION

The present invention relates to tyrosine phosphatases. In particular, the invention concerns a new family of phosphatase proteins, nucleotide sequences encoding these proteins, various products and assay method that can be used for identifying compounds useful for the diagnosis and treatment of various PTP-related diseases and conditions, for example cell pproliferative disorders. Two family members have been identified which we have called PTP05 and PTP10.

BACKGROUND OF THE INVENTION

The following description is provided to aid in understanding the invention but is not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function. The best characterized protein kinases in eukaryotes phosphorylate proteins on the alcohol moiety of serine, threonine and tyrosine residues. These kinases largely fall into two groups, those specific for phosphorylating serines and threonines, and those specific for phosphorylating tyrosines.

The phosphorylation state of a given substrate is also regulated by a class of proteins responsible for removal of the phosphate group added to a given substrate by a protein kinase. The protein phosphatases can also be classified as being specific for either serine/threonine or tyrosine. The known enzymes can be divided into two groups—receptor and non-receptor type proteins. Most receptor-type protein tyrosine phosphatases (RPTPs) contain two conserved catalytic tyrosine phosphatase domains each of which encompasses a segment of 240 amino acid residues (Saito et al., *Cell Growth and Diff.* 2:59–65, 1991). The RPTPs can be subclassified further based upon the amino acid sequence diversity of their extracellular domains (Saito, et al., supra; Krueger, et al., *Proc. Natl. Acad. Sci. USA* 89:7417–7421, 1992). Alignment of primary peptide sequences of both types of known PTPases shows some sequence consensus in catalytic domains and has made it possible to identify cDNAs encoding proteins with tyrosine phosphate activity via the polymerase chain reaction (PCR).

Many kinases and phosphatases are involved in regulatory cascades wherein their substrates may include, but are not limited to, other kinases and phosphatases whose activities are regulated by their phosphorylation state. Ultimately the activity of some downstream effector is modulated by phosphorylation resulting from activation of such a pathway.

It is well established that the abnormal or inappropriate activity of tyrosine kinases and/or tyrosine phosphatases plays a role in a variety of human disorders including cell proliferative disorders such as cancer, fibrotic disorders, disorders of the immune system and metabolic disorders such as diabetes. A need, therefore, exists to identify new tyrosine kinases and phosphatases as a first step in understanding a disease process and the subsequent identification of therapeutic treatments for the disorder.

SUMMARY OF THE INVENTION

Disclosed herein is a family of tyrosine phosphatases expressed in hematopoietic cells, two members of which we have named PTP05 and PTP10. The properties of these phosphatases are described below. The present invention concerns PTP05 and PTP10 polypeptides, nucleic acids encoding such polypeptides, cells, tissues and animals containing such nucleic acids, antibodies to the polypeptides, assays utilizing the polypeptides, and methods relating to all of the foregoing.

A first aspect of the invention features an isolated, enriched, or purified nucleic acid molecule encoding a PTP05 or a PTP10 polypeptide.

By "isolated" in reference to nucleic acid it is meant a polymer of 14, 17, 21 or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90–95% pure at least) of non-nucleotide material naturally associated with it and thus is meant to be distinguished from isolated chromosomes.

By the use of the term "enriched" in reference to nucleic acid it is meant that the specific DNA or RNA sequence constitutes a significantly higher fraction (2–5) fold of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$ fold purification of the native message. Thus, purification of at least one order of magnitude, preferably two or three orders, and more preferably four or five orders of magnitude is expressly contemplated. The term is also chosen to distinguish clones already in existence which may encode PTP05 or PTP10 but which have not been isolated from other clones in a library of clones. Thus, the term covers clones encoding PTP05 or PTP10 which are isolated from other non-PTP05 clones or non-PTP10 clones.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA. The probe hybridizes (binds) to complementary sequences of cDNA.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

The term "hybridize" refers to a method of interacting a nucleic acid sequence with a DNA or RNA molecule in solution or on a solid support, such as cellulose or nitrocellulose. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Under highly stringent hybridization conditions only highly complementary nucleic acid sequences hybridize. Preferably, such conditions prevent hybridization of nucleic acids having one or two mismatches out of 20 contiguous nucleotides.

Various low or high stringency hybridization conditions may be used depending upon the specificity and selectivity desired. Stringency is controlled by varying salt or denaturant concentrations. Examples of hybridization conditions are shown in the examples below. High stringent conditions may mean conditions that are at least as stringent as the following: hybridization in 50% formamide, 5×SSC, 50 mM NaH$_3$PO$_4$, pH 6.8, 0.5% SDS, 0.1 mg/mL sonicated salmon sperm DNA, and 5× Denhart solution at 42° C. overnight; washing with 2×SSC, 0.1% SDS at 45° C.; and washing with 0.2×SSC, 0.1% SDS at 45° C. Those skilled in the art will recognize how such conditions can be varied to vary specificity and selectivity.

A PTP05 or PTP10 polypeptide can be encoded by a full-length nucleic acid sequence or any portion of the full-length nucleic acid sequence. In preferred embodiments the isolated nucleic acid comprises, consists essentially of, or consists of a nucleic acid sequence set forth in SEQ ID NO:1, SEQ ID NO:2, SEQ ID NO:3, or SEQ ID NO:4, a nucleic acid sequence that hybridizes to the nucleic acid sequence set forth in SEQ ID NO:1, SEQ ID NO:2, SEQ ID NO:3, or SEQ ID NO:4, or a functional derivative (as defined below) of either of the foregoing. The nucleic acid may be isolated from a natural source by cDNA cloning or subtractive hybridization; the natural source may be mammalian (human) blood, semen, or tissue and the nucleic acid may be synthesized by the triester or other method or by using an automated DNA synthesizer.

In other preferred embodiments, the nucleic acid molecule of the invention comprises a nucleotide sequence that (a) encodes a polypeptide having the full length amino acid sequence set forth in SEQ ID NO:2; (b) is the complement of the nucleotide sequence of (a); (c) hybridizes under highly stringent conditions to the nucleotide molecule of (a) and encodes a naturally occurring PTP05 or PTP10 polypeptide; (d) encodes a PTP05 or a PTP10 polypeptide having the full length amino acid sequence of the sequence set forth in SEQ ID NO:5, SEQ ID NO:6, SEQ ID NO:7, or SEQ ID NO:8 except that it lacks one or more of the following segments of amino acid residues: 1–187, 188–420, 421–426 of SEQ ID NO:5, 44–80, 225–457, 458–463 of SEQ ID NO:6, or 1–87, 188–405, 406–412 of SEQ ID NO:7; (e) is the complement of the nucleotide sequence of (d); (f) encodes a polypeptide having the amino acid sequence set forth in SEQ ID NO:5, SEQ ID NO:6, SEQ ID NO:7, or SEQ ID NO:8 from amino acid residues 1–187, 188–420, 421–426 of SEQ ID NO:5, 44–80, 225–457, 458–463 of SEQ ID NO:6, or 1–87, 188–405, 406–412 of SEQ ID NO:7; (g) is the complement of the nucleotide sequence of (f); (h) encodes a polypeptide having the full length amino acid sequence set forth in SEQ ID NO:5, SEQ ID NO:6, SEQ ID NO:7, or SEQ ID NO:8 except that it lacks one or more of the domains selected from the group consisting of an N-terminal domain, a catalytic domain, and a C-terminal domain; or (i) is the complement of the nucleotide sequence of (h). The nucleic acid molecule of the invention is isolated, enriched, or purified from, preferably, a mammal, or most preferably from a human.

In yet other preferred embodiments the nucleic acid is an isolated conserved or unique region, for example those useful for the design of hybridization probes to facilitate identification and cloning of additional polypeptides, or for the design of PCR probes to facilitate cloning of additional polypeptides.

By "conserved nucleic acid regions", it is meant regions present on two or more nucleic acids encoding an PTP05 polypeptide, to which a particular nucleic acid sequence can hybridize under lower stringency conditions. Examples of lower stringency conditions suitable for screening for nucleic acids encoding PTP05 polypeptides are provided in Abe, et al. *J. Biol. Chem.* 19:13361 (1992) (hereby incorporated by reference herein in its entirety, including any drawings). Preferably, conserved regions differ by no more than 5 out of 20 contiguous nucleotides.

By "unique nucleic acid region" it is meant a sequence present in a full length nucleic acid coding for a PTP05 polypeptide or a PTP10 polypeptide that is not present in a sequence coding for any other known naturally occurring polypeptide. Such regions preferably comprise 14, 17, 21 or more contiguous nucleotides present in the full length nucleic acid encoding a PTP05 polypeptide or a PTP10 polypeptide. In particular, a unique nucleic acid region is preferably of human origin.

In yet another aspect, the invention relates to a nucleic acid vector comprising a nucleic acid molecule encoding a PTP05 or a PTP10 polypeptide and a promoter element effective to initiate transcription in a host cell.

The term "nucleic acid vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. The terms "transformation" and "transfection" refer to methods of inserting an expression construct into a cellular organism. These methods involve a variety of techniques, such as treating the cells with high concentrations of salt, an electric field, or detergent, to render the host cell outer membrane or wall permeable to nucleic acid molecules of interest.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the PTP05 or a PTP10 nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the PTP05 or PTP10 nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

The invention also features a nucleic acid probe for the detection of a nucleic acid encoding a PTP05 polypeptide or a PTP10 polypeptide in a sample.

The nucleic acid probe contains nucleic acid that will hybridize to a sequence of at least 14 contiguous nucleotides set forth in SEQ ID NO:1 or SEQ ID NO:2 or a functional derivative thereof. The probe is preferably at least 14, 17 or more bases in length and selected to hybridize specifically to a unique region of a PTP05 or a PTP10 encoding nucleic acid.

In preferred embodiments the nucleic acid probe hybridizes to nucleic acid encoding at least 14 contiguous amino acids of the sequences set forth in SEQ ID NO:1, SEQ ID NO:2, SEQ ID NO:3, or SEQ ID NO:4, or a functional derivative thereof. Various low or high stringency hybridization conditions may be used depending upon the specificity and selectivity desired. Under highly stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount of PTP05 RNA or PTP10 RNA in a sample by contacting the sample with a nucleic acid probe under conditions such that hybridization occurs and detecting the presence or amount of the probe bound to PTP05 RNA or PTP10 RNA. The nucleic acid duplex formed between the probe and a nucleic acid sequence coding for a PTP05 polypeptide or a PTP10 polypeptide may be used in the identification of the sequence of the nucleic acid detected (for example see, Nelson et al., in Nonisotopic DNA Probe Techniques, p. 275 Academic Press, San Diego (Kricka, ed., 1992) hereby incorporated by reference herein in its entirety, including any drawings). Kits for performing such methods may be constructed to include a container having disposed therein a nucleic acid probe.

Another feature of the invention is a nucleic acid molecule as set forth in SEQ ID NO:1, SEQ ID NO:2, SEQ ID NO:3, or SEQ ID NO:4 or fragments thereof, comprising one or more regions that encode a PTP05 or a PTP10 polypeptide or a PTP05 or a PTP10 domain polypeptide, where the PTP05 or PTP10 polypeptide or the PTP05 or PTP10 domain polypeptide is fused to a non-PTP05 or non-PTP10 polypeptide. Such fused polypeptides include, for example, but are not limited to, a GST-fusion protein.

The invention also features recombinant nucleic acid, preferably in a cell or an organism. The recombinant nucleic acid may contain a sequence set forth in SEQ ID NO:1, SEQ ID NO:2, SEQ ID NO:3, or SEQ ID NO:4 or a functional derivative thereof and a vector or a promoter effective to initiate transcription in a host cell. The recombinant nucleic acid can alternatively contain a transcriptional initiation region functional in a cell, a sequence complimentary to an RNA sequence encoding a PTP05 polypeptide or a PTP10 polypeptide and a transcriptional termination region functional in a cell.

Another aspect of the invention relates to a recombinant cell or tissue comprising a nucleic acid molecule encoding a PTP05 or PTO10 polypeptide. The recombinant cell may comprise a nucleic acid molecule encoding either a PTP05 polypeptide; a PTP10 domain polypeptide; or a PTP10 polypeptide or PTP10 domain polypeptide fused to a non-PTP10 polypeptide.

The term "recombinant organism" refers to an organism that has a new combination of genes or nucleic acid molecules. A new combination of genes or nucleic acid molecules can be introduced to an organism using a wide array of nucleic acid manipulation techniques available to those skilled in the art.

The term "organism" relates to any living being comprised of a least one cell. An organism can be as simple as one eukaryotic cell or as complex as a mammal. Therefore, a recombinant organism can also be a recombinant cell, which may be a eukaryotic or a prokaryotic organism.

The term "eukaryote" refers to an organism comprised of cells that contain a nucleus. Eukaryotes are differentiated from "prokaryotes" which do not have a nucleus and lack other cellular structures found in eukaryotes, such as mitochondria and endoplasmic reticulum. Prokaryotes include unicellular organisms, such as bacteria, while eukaryotes are represented by yeast, invertebrates, and vertebrates.

The recombinant cell can harbor a nucleic acid vector that is extra genomic. The term "extragenomic" refers to a nucleic acid vector which does not insert into the cell genome. Many nucleic acid vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell. Thus these vectors replicate independently of the host genome and do not recombine with or integrate into the genome.

A recombinant cell can harbor a portion of a nucleic acid vector in an intra genomic fashion. The term "intragenomic" defines a nucleic acid construct that is incorporated within the cell genome. Multiple nucleic acid vectors available to those skilled in the art contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

Another aspect of the invention features an isolated, enriched, or purified PTP05 polypeptide or an isolated, enriched, or purified PTP10 polypeptide.

By "PTP05 polypeptide" or "PTP10 polypeptide" it is meant an amino acid sequence substantially similar to the sequence shown in SEQ ID NO:5, SEQ ID NO:6, SEQ ID NO:7 or SEQ ID NO:8, or fragments thereof. A sequence that is substantially similar will preferably have at least 90% identity (more preferably at least 95% and most preferably 99–100%) to the sequence of SEQ ID NO:5, SEQ ID NO:6, SEQ ID NO:7 or SEQ ID NO:8.

The PTP05 or PTP10 polypeptides of the present invention preferably have a substantially similar biological activity to the protein encoded by the full length nucleic acid sequence set forth in SEQ ID NO:1, SEQ ID NO:2, SEQ ID NO:3, or SEQ ID NO:4 or to SEQ ID NO:1 the proteins with amino acid sequence set forth in SEQ ID NO:5, SEQ ID NO:6, SEQ ID NO:7, or SEQ ID NO:8. By "biological activity" it is meant an activity of the PTP10 protein in a cell. The biological activity of the PTP10 is related to some of the activities of the cell which include, but are not limited to, cell proliferation motogenesis, metastasis, tumor escape, cell adhesion, transformation, or apoptosis.

By "identity" is meant a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

By "isolated" in reference to a polypeptide is meant a polymer of 6, 12, 18 or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of material naturally associated with it.

By the use of the term "enriched" in reference to a polypeptide it is meant that the specific amino acid sequence constitutes a significantly higher fraction (2–5 fold) of the total of amino acids present in the cells or solution of interest than in normal or diseased cells or in the cells from which the sequence was taken. This could be caused-by a person by preferential reduction in the amount of other amino acid sequences present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased.

The term "significant" here is used to indicate that the level of increase is useful to the person making such an increase, and generally means an increase relative to other amino acid sequences of about at least 2 fold, more preferably at least 5 to 10 fold or even more. The term also does not imply that there are no amino acid sequences from other sources. The other source amino acid may, for example, comprise amino acid encoded by a yeast or bacterial genome, or a cloning vector such as pUC19. The term is meant to cover only those situations in which a person has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/mL). Purification of at least one order of magnitude, preferably two or three orders, and more preferably four or five orders of magnitude is expressly contemplated. The substance is preferably free of contamination at a functionally significant level, for example 90%, 95%, or 99% pure.

In another aspect the invention features an isolated, enriched, or purified PTP05 polypeptide fragment or a PTP10 polypeptide fragment.

By "a PTP05 polypeptide fragment" or "PTP10 polypeptide fragment" it is meant an amino acid sequence that is less than the full-length amino acid sequence. The full-length amino acid sequences of three PTP05 isoforms are shown in SEQ ID NO:5, SEQ ID NO:6 and SEQ ID NO:7. Examples of fragments include PTP05 domains, PTP05 mutants and PTP05-specific epitopes and PTP10 domains, PTP10 mutants and PTP10-specific epitopes.

By "a PTP05 domain" or a "PTP10 domain" it is meant a portion of the PTP05 polypeptide or the PTP10 polypeptide having homology to amino acid sequences from one or more known proteins wherein the sequence predicts some common function, interaction or activity. Well known examples of domains are the SH2 (Src Homology 2) domain (Sadowski, et al., *Mol. Cell. Biol.* 6:4396, 1986; Pawson and Schlessinger, *Curr. Biol.* 3:434, 1993), the SH3 domain (Mayer, et al., *Nature* 332:272, 1988; Pawson and Schlessinger, *Curr. Biol.* 3:434, 1993), and pleckstrin (PH) domain (Ponting, *TIBS* 21:245, 1996; Haslam, et al., *Nature* 363:309, 1993), all of which are domains that mediate protein:protein interaction or protein:lipid interaction, and the kinase catalytic domain (Hanks and Hunter, *FASEB J.* 9:576–595, 1995). Computer programs designed to detect such homologies are well known in the art. The relative homology is at least 20%, more preferably at least 30% and most preferably at least 35%.

By a "PTP05 mutant" or "PTP10 mutant" it is meant a PTP05 polypeptide or PTP10 polypeptide which differs from the native sequence in that one or more amino acids have been changed, added or deleted. Changes in amino acids may be conservative or non-conservative. By "conservative" it is meant the substitution of an amino acid for one with similar properties such as charge, hydrophobicity, structure, etc. Examples of polypeptides encompassed by this term include, but are not limited to, (1) chimeric proteins which comprise a portion of a PTP05 polypeptide or PTP10 polypeptide sequence fused to a non-PTP05 or non-PTP10 polypeptide sequence, for example a polypeptide sequence of hemagglutinin (HA), (2) PTP05 or PTP10 proteins lacking a specific domain, for example the catalytic domain, and (3) PTP05 or PTP10 proteins having a point mutation. A PTP05 mutant or PTP10 mutant will retain some useful function such as, for example, binding to a natural binding partner, catalytic activity, or the ability to bind to a PTP05 specific antibody or a PTP10 specific antibody (as defined below).

By "PTP05-specific epitope" or "PTP10-specific epitope" it is meant a sequence of amino acids that is both antigenic and unique to PTP05 or to PTP10, respectively. A PTP05-specific epitope can be used to produce PTP05-specific antibodies and a PTP10-specific epitope can be used to produce PTP10-specific antibodies, as more fully described below. Particularly preferred epitopes a shown in the Examples section below.

By "recombinant PTP05 polypeptide" or "recombinant PTP10 polypeptide" it is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

The polypeptide of the invention comprises an amino acid sequence having (a) the full length amino acid sequence set forth in SEQ ID NO:5, SEQ ID NO:6, SEQ ID NO:7, or SEQ ID NO:8; (b) the full length amino acid sequence of the sequence set forth in SEQ ID NO:5, SEQ ID NO:6, SEQ ID NO:7, or SEQ ID NO:8, except that it lacks one or more of the following segments of amino acid residues: 1–187, 188–420, 421–426 of SEQ ID NO:5, 44–80, 225–457, 458–463 of SEQ ID NO:6, or 1–87, 188–405, 406–412 of SEQ ID NO:7; (c) the amino acid sequence set forth in SEQ ID NO:5, SEQ ID NO:6, SEQ ID NO:7, or SEQ ID NO:8 from amino acid residues 1–187, 188–420, 421–426 of SEQ ID NO:5, 44–80, 225–457, 458–463 of SEQ ID NO:6, or 1–87, 188–405, 406–412 of SEQ ID NO:7; or (d) the full length amino acid sequence set forth in SEQ ID NO:5, SEQ ID NO:6, SEQ ID NO:7, or SEQ ID NO:8 except that it lacks one or more of the domains selected from the group consisting of an N-terminal domain, a catalytic domain, and a C-terminal domain.

In yet another aspect the invention features an antibody (e.g., a monoclonal or polyclonal antibody) having specific binding affinity to a PTP05 or PTP10 polypeptide or PTP05 or PTP10 polypeptide fragment. By "specific binding affinity" is meant that the antibody binds to target (PTP05 or PTO10) polypeptides with greater affinity than it binds to other polypeptides under specified conditions. Antibodies having specific binding affinity to a PTP05 or a PTP10 polypeptide may be used in methods for detecting the presence and/or amount of a PTP05 or PTP10 polypeptide in a sample by contacting the sample with the antibody under conditions such that an immunocomplex forms and detecting the presence and/or amount of the antibody conjugated to the PTP05 or PTP10 polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., *Nature* 256:495–497 (1975), and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In another aspect the invention features a hybridoma which produces an antibody having specific binding affinity to a PTP05 polypeptide or a hybridoma which produces an antibody having specific binding affinity to a PTP10 polypeptide. By "hybridoma" is meant an immortalized cell line which is capable of secreting an antibody, for example a PTP05 antibody or a PTP10 antibody. In preferred embodiments the PTP05 antibody comprises a sequence of amino acids that is able to specifically bind a PTP05 polypeptide, and the PTP10 antibody comprises a sequence of amino acids that is able to specifically bind a PTP10 polypeptide.

The invention features a method for identifying human cells containing a PTP05 polypeptide, a PTP10 polypeptide or a related sequence. The method involves identifying the novel polypeptide in human cells using techniques that are routine and standard in the art, such as those described herein for identifying PTP05 (e.g., cloning, Southern or Northern blot analysis, in situ hybridization, PCR amplification, etc.).

The invention also features methods of screening cells for natural binding partners of PTP05 polypeptides or PTP10 polypeptides. By "natural binding partner" it is meant a protein that interacts with PTP05 or with PTP10. Binding partners include ligands, agonists, antagonists and downstream signaling molecules such as adaptor proteins and may be identified by techniques well known in the art such as co-immunoprecipitation or by using, for example, a two-hybrid screen. (Fields and Song, U.S. Pat. No. 5,283,173, issued Feb. 1, 1994 and, incorporated be reference herein.) The present invention also features the purified, isolated or enriched versions of the polypeptides identified by the methods described above.

In another aspect, the invention provides a method for identifying a substance capable of modulating PTO05 or PTP10 activity comprising the steps of (a) contacting a PTO05 or PTP10 polypeptide with a test substance; and (b) determining whether the substance alters the activity of said polypeptide.

The invention also features another method of identifying substances capable of modulating the function of a PTO05 or PTP10 polypeptide. The method comprises the following steps: (a) expressing a PTO05 or PTP10 polypeptide in cells; (b) adding a compound to the cells; and (c) monitoring a change or an absence of a change in cell phenotype, cell proliferation, catalytic activity of the PTO05 or PTP10 polypeptide, and binding a natural binding partner.

The term "compound" includes small organic molecules including, but not limited to, oxindolinones, quinazolines, tyrphostins, quinoxalines, and those contained within extracts from natural sources. Examples of such compounds are included in section XII, below.

The term "function" refers to the cellular role of a serine-threonine protein kinase. The serine-threonine protein kinase family includes members that regulate many steps in signaling cascades, including cascades controlling cell growth, migration, differentiation, gene expression, muscle contraction, glucose metabolism, cellular protein synthesis, and regulation of the cell cycle.

The term "modulates" refers to the ability of a compound to alter the function of a protein kinase. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "catalytic activity," in the context of the invention, defines the ability of a protein kinase to phosphorylate a substrate. Catalytic activity can be measured, for example, by determining the amount of a substrate converted to a product as a function of time. Phosphorylation of a substrate occurs at the active-site of a protein kinase. The active-site is normally a cavity in which the substrate.

The term "substrate" as used herein refers to a molecule that is phoshorylated by or directly interacts with the protein kinase. The substrate is preferably a peptide and more preferably a protein. For example, in relation to the protein kinase RAF, preferred substrates are MEK and the MEK substrate MAPK.

The term "activates" refers to increasing the cellular function of a protein kinase. The protein kinase function is preferably the interaction with a natural binding partner or catalytic activity.

The term "inhibit" refers to decreasing the cellular function of a protein kinase. The protein kinase function is preferably the interaction with a natural binding partner or catalytic activity.

The term "modulates" also refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner.

The term "complex" refers to an assembly of at least two molecules bound to one another. Signal transduction complexes often contain at least two protein molecules bound to one another, either transiently or in succession. For instance, a receptor protein tyrosine kinase, GRB2, SOS, and RAF sequentially interact in response to a mitogenic ligand.

The term "expressing" as used herein refers to the production of a PTO05 or PTP10 polypeptide from a nucleic acid vector containing a PTO05 or PTP10 gene within a cell. The nucleic acid vector is transfected into cells using well known techniques in the art as described herein.

The term "adding" as used herein refers to administering a solution comprising a compound to the medium bathing cells. The solution comprising the compound can also comprise an agent, such as dimethyl sulfoxide, which facilitates the uptake of the compound into the cells.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "cell phenotype" refers to the outward appearance of a cell or tissue or the function of the cell or tissue. Examples of cell or tissue phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Change or the absence of change in cell phenotype is readily measured by techniques known in the art.

The term "cell proliferation" refers to the rate at which a group of cells divides. The number of cells growing in a vessel can be quantitated by a person skilled in the art when that person visually counts the number of cells in a defined area using a common light microscope. Alternatively, cell proliferation rates can be quantitated by laboratory apparatae that optically measure the density of cells in an appropriate medium.

The method can utilize any of the molecules disclosed in the invention. These molecules include nucleic acid molecules encoding PTO05 or PTP10 polypeptides, nucleic acid vectors, recombinant cells, polypeptides, or antibodies of the invention.

In a preferred embodiment, the invention provides a method for treating or preventing an abnormal condition by administering a compound which is a modular of PTO05 or PTP10 function in vitro. The abnormal condition preferably involves abnormality in PTO05 or PTP10 signal transduction pathway, and most preferably is cancer. Such compounds preferably show positive results in one or more in vitro assays for an activity corresponding to treatment of the disease or disorder in question (such as the assays described in Example 6 below). Examples of substances that can be screened for favorable activity are provided in section XII below.

The summary of the invention described above is non-limiting and other features and advantages of the invention will be apparent from the following detailed description, and from the claims.

DESCRIPTION OF FIGURES

FIG. 1 shows a computer generated alignment between the nucleic acid (FIG. 1A) and amino acid (FIG. 1B) sequences from the catalytic domains of PTP05 and PTP10. As can be seen from the alignments, PTP05 and PTP10 are highly related at both the nucleic acid (92%) and amino acid (85%) level, suggesting they are members of a family of PTPs.

DETAILED DESCRIPTION OF THE INVENTION

The present invention relates to a new family of tyrosine phosphatases and the isolation and characterization of two members of this family, proteins which we have called PTP05 and PTP10, nucleotide sequences encoding PTP05 and PTP10, various products and assay methods that can be used to identify compounds useful for the diagnosis and treatment of various PTP05 and PTP10 related diseases and conditions, for example diabetes. Polypeptides derived from PTP05 and PTP10 and nucleic acids encoding such polypeptides may be produced using well known and standard synthesis techniques when given the sequences presented herein.

PTP05 is a tyrosine phosphatase with an apparent molecular weight of approximately 49 kDa. Two additional isoforms have been identified, one larger (approximately 54 kDa) and one smaller (approximately 47 kDa). Primary sequence analysis shows that PTP05 is comprised of three domains: an N-terminal domain, a catalytic domain, and a C-terminal domain. The lack of a hydrophobic stretch of amino acids generally characterized as a transmembrane region indicates that PTP05 is a non-receptor tyrosine phosphatase. PTP10 is also a tyrosine phosphatase with significant homology to PTP05. Together they define a new family of PTPs.

The polypeptide and nucleotide sequences of the invention can be used, for example, to generate antibodies for use as diagnostic kits, or to create recombinant cell lines that can be used to identify modulators of PTP05 or PTP10 activity. Moreover, the sequences of the invention can be used to obtain full-length sequences of PTP05 and/or PTP10 from additional species, in particular humans, using techniques well known in the art and also described below.

I. Nucleic Acids Encoding PTP05 and/or PTP10 Polypeptides

A first aspect of the invention features nucleic acid sequences encoding a PTP05 polypeptide or a PTP10 polypeptide. Included within the scope of this invention are the functional equivalents of the herein-described isolated nucleic acid molecules. Functional equivalents or derivatives can be obtained in several ways. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the PTP05 gene could be synthesized to give a nucleic acid sequence significantly different from that shown in SEQ ID NO:1, SEQ ID NO:2, or SEQ ID NO:3. Likewise portions or all of the PTP10 gene could be synthesized to give a nucleic acid sequence significantly different from that shown in SEQ ID NO:4. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1, SEQ ID NO: 2, SEQ ID NO:3, or SEQ ID NO:4, or a derivative thereof. Any nucleotide or polynucleotide may be used in this regard, provided that its addition, deletion or substitution does not alter the amino acid sequence of SEQ ID NO:5, SEQ ID NO:6, or SEQ ID NO:7, or SEQ ID NO:8 which is encoded by the nucleotide sequence. For example, the present invention is intended to include any nucleic acid sequence resulting from the addition of ATG as an initiation codon at the 5'-end of a PTP05 or PTP10 nucleic acid sequence or its functional derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the PTP05 genes, PTP10 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

Functional equivalents or derivatives of PTP05 or PTP10 can also be obtained using nucleic acid molecules encoding one or more functional domains of the PTP05 polypeptide or the PTP10 polypeptide, respectively. For example, the catalytic domain of PTP05 functions to remove phosphate molecules bound onto tyrosine residues and a nucleic acid sequence encoding the catalytic domain alone or linked to other heterologous nucleic acid sequences can be considered a functional derivative of PTP05. Other functional domains of these proteins include, but are not limited to, the proline-rich region within the N-terminal domain, and the C-terminal domain. Nucleic acid sequences encoding these domains are shown in SEQ ID NO:1 as follows: N-terminal domain approximately 199–759; catalytic domain approximately 760–1458, C-terminal domain approximately 1459–1476.

II. A Nucleic Acid Probe for the Detection of PTP05 or PTP10

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (e.g. "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond topU N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "PCR Protocols, A Guide to Methods and Applications", edited by Innis et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (e.g. "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA as well as DNA probes and nucleic acids modified in the sugar, phosphate or even the base portion as long as the probe still retains the ability to specifically hybridize under conditions as disclosed herein. Such probes are generated using techniques known in the art. The nucleic acid probe may be immobilized on a solid support. Examples of such solid supports include, but are not limited to, plastics such as polycarbonate, complex carbohydrates such as agarose and sepharose, acrylic resins, such as polyacrylamide and latex beads, and nitrocellulose. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. A Probe Based Method and Kit for Detecting PTP05 or PTP10

One method of detecting the presence of PTP05 or PTP10 in a sample comprises (a) contacting the sample with one of the above-described nucleic acid probes, under conditions such that hybridization occurs, and (b) detecting the presence of the probe bound to a nucleic acid molecule in the sample. One skilled in the art would select the nucleic acid probe according to techniques known in the art as described above. Samples to be tested include but should not be limited to RNA samples of human tissue.

A kit for detecting the presence of PTP05 or PTP10 in a sample comprises at least one container having disposed therein an above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatically labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

IV. DNA Constructs Comprising a PTP05 Nucleic Acid Molecule or PTP10 Nucleic Acid Molecule and Cells Containing These Constructs The present invention also relates to a recombinant DNA molecule comprising, 5' to 3', a promoter effective to initiate transcription in a host cell and one of the above-described nucleic acid molecules. In addition, the present invention relates to a recombinant DNA molecule comprising a vector and a nucleic acid molecule described herein. The present invention also relates to a nucleic acid molecule comprising a transcriptional region functional in a cell, a sequence complimentary to an RNA sequence encoding an amino acid sequence corresponding to a PTP05 polypeptide, a PTP10 polypeptide or functional derivative of either, and a transcriptional termination region functional in said cell. The above-described molecules may be isolated and/or purified DNA molecules.

The present invention also relates to a cell or organism that contains a PTP05 nucleic acid molecule or a PTP10 nucleic acid molecule, as described herein, and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but will in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a PTP05 gene or a PTP10 gene may be obtained by the above-described cloning methods. This region may be retained for its transcriptional termination regulatory sequences, such as termination and polyadenylation. Thus, by retaining the 3'-region naturally contiguous to the DNA sequence encoding a PTP05 gene or a PTP10 gene, the transcriptional termination signals may be provided. Where the transcriptional termination signals are not satisfactorily functional in the expression host cell, then a 3' region functional in the host cell may be substituted.

Two DNA sequences (such as a promoter region sequence and a PTP05 sequence) are said to be operably linked if the nature of the linkage between the two DNA sequences does not (1) result in the introduction of a frame-shift mutation, (2) interfere with the ability of the promoter region sequence to direct the transcription of the second sequence, for example a PTP05 gene sequence, or (3) interfere with the ability of the second sequence to be transcribed by the promoter region sequence. Thus, a promoter region would be operably linked to a DNA sequence if the promoter were capable of effecting transcription of that DNA sequence. Thus, transcriptional and translational signals recognized by an appropriate host are necessary to express a PTP05 gene or PTP10 gene.

The present invention encompasses the expression of a PTP05 gene, a PTP10 gene (or a functional derivative thereof) in either prokaryotic or eukaryotic cells. Prokaryotic hosts are, generally, very efficient and convenient for the production of recombinant proteins and are, therefore, one type of preferred expression system for these genes. Prokaryotes most frequently are represented by various strains of E. coli. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include lgt10, lgt11 and the like; and suitable virus vectors may include pMAM-neo, PKRC and the like. Preferably, the selected vector of the present invention has the capacity to replicate in the selected host cell.

Recognized prokaryotic hosts include bacteria such as E. coli and those from genera such as Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express PTP05 or PTP10 (or a functional derivative thereof) in a prokaryotic cell, it is necessary to operably link the gene sequence to a functional prokaryotic promoter. Such promoters may be either constitutive or, more preferably, regulatable (i.e., inducible or derepressible). Examples of constitutive promoters include the int promoter of bacteriophage 1, the bla promoter of the b-lactamase gene sequence of pBR322, and the CAT promoter of the chloramphenicol acetyl transferase gene sequence of pPR325, and the like. Examples of inducible prokaryotic promoters include the major right and left promoters of bacteriophage 1 ($P_L$ and $P_R$), the trp, recA, lacZ, lacI, and gal promoters of E. coli, the a-amylase (Ulmanen et al., J. Bacteriol. 162:176–182, 1985) and the sigma-28-specific promoters of B. subtilis (Gilman et al., Gene Sequence 32:11–20(1984)), the promoters of the bacteriophages of Bacillus (Gryczan, In: The Molecular Biology of the Bacilli, Academic Press, Inc., NY (1982)), and Streptomyces promoters (Ward et al., Mol. Gen. Genet. 203:468–478, 1986). Prokaryotic promoters are reviewed by Glick (J. Ind. Microbiot. 1:277–282, 1987); Cenatiempo (Biochimie 68:505–516, 1986); and Gottesman (Ann. Rev. Genet. 18:415–442, 1984).

Proper expression in a prokaryotic cell also requires the presence of a ribosome binding site upstream of the gene sequence-encoding sequence. Such ribosome binding sites are disclosed, for example, by Gold et al. (Ann. Rev. Microbiol. 35:365–404, 1981). The selection of control sequences, expression vectors, transformation methods, and the like, are dependent on the type of host cell used to express the gene.

As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the PTP peptide of interest. Suitable hosts may often include eukaryotic cells. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO, 3T3 or CHO-K1, or cells of lymphoid origin (such as 32D cells) and their derivatives. Preferred mammalian host cells include SP2/0 and J558L, as well as neuroblastoma cell lines such as IMR 332 and PC12 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, Science 240:1453–1459, 1988). Alternatively, baculovirus vectors can be engineered to express large amounts of PTP05 or PTP10 in insects cells (Jasny, Science 238:1653, 1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of PTP05 or PTP10.

A particularly preferred yeast expression system is that utilizing schizosaccharmocyces pombe. This system is useful for studying the activity of members of the Src family (Superti-Furga, et al, EMBO J. 12:2625, 1993) and other non-receptor-TKs, the function of which is often regulated by the activity of tyrosine phosphatases.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of PTP05 or PTP10 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288, 1982); the TK promoter of Herpes virus (McKnight, *Cell* 31:355–365, 1982); the SV40 early promoter (Benoist et al., *Nature (London)* 290:304–310, 1981); the yeast gal4 gene sequence promoter (Johnston et al., *Proc. Natl. Acad. Sci. (USA)* 79:6971–6975, 1982); Silver et al., *Proc. Natl. Acad. Sci. (USA)* 81:5951–5955, 1984).

Translation of eukaryotic mRNA is initiated at the codon which encodes the first methionine. For this reason, it is preferable to ensure that the linkage between a eukaryotic promoter and a DNA sequence which encodes PTP05 or PTP10 (or a functional derivative thereof) does not contain any intervening codons which are capable of encoding a methionine (i.e., AUG). The presence of such codons results either in the formation of a fusion protein (if the AUG codon is in the same reading frame as the coding sequence) or a frame-shift mutation (if the AUG codon is not in the same reading frame as a PTP05 coding sequence).

A PTP05 nucleic acid molecule or PTP10 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule (a plasmid). Since such molecules are incapable of autonomous replication, the expression of the gene may occur through the transient expression of the introduced sequence. Alternatively, permanent or stable expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototropy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Mol. Cell. Bio.* 3:280, 1983.

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColE1, pSC101, PACYC 184, pVX. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, NY (1982), pp. 307–329). Suitable Streptomyces plasmids include pIJ101 (Kendall et al., *J. Bacteriol.* 169:4177–4183, 1987), and streptomyces bacteriophages such as fC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704, 1986), and Izaki (*Jpn. J. Bacteriol.* 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982); Broach, In: "The Molecular Biology of the Yeast Saccharomyces: Life Cycle and Inheritance", Cold Spring Harbor Laboratory, Cold Spring Harbor, N.Y., p. 445–470 (1981); Broach, *Cell* 28:203–204, 1982); Bollon et al., J. *Clin. Hematol. Oncol.* 10:39–48, 1980); Maniatis, In: Cell Biology: A Comprehensive Treatise, Vol. 3, *Gene Sequence Expression*, Academic Press, NY, pp. 563–608 (1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct micro injection, and the like. After the introduction of the vector, recipient cells are grown in a selective medium, which selects for the growth of vector-containing cells. Expression of the cloned gene molecule(s) results in the production of PTP05, PTP10 or fragments or functional derivatives thereof of either. This can take place in the transformed cells as such, or following the induction of these cells to differentiate (for example, by administration of bromodeoxyuracil to neuroblastoma cells or the like). A variety of incubation conditions for the transformed cells can be used to foster expression of the polypeptides of the present invention. The most preferred conditions are those which mimic physiological conditions.

V. PTP05 and PTP10 Polypeptides

Also a feature of the invention are PTP05 and PTP10 polypeptides. A variety of methodologies known in the art can be utilized to obtain the polypeptides of the present invention. They may be purified from tissues or cells which naturally produce them. Alternatively, the above-described isolated nucleic acid sequences can be used to express the proteins of the invention recombinantly.

Any eukaryotic organism can be used as a source for the polypeptide of the invention, as long as the source organism naturally contains such a polypeptide. As used herein, "source organism" refers to the original organism from which the amino acid sequence is derived, regardless of the organism the protein is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

A PTP05 and PTP10 proteins, like all proteins, are comprised of distinct functional units or domains. In eukaryotes, proteins sorted through the so-called vesicular pathway (bulk flow) usually have a signal sequence (also called a leader peptide) in the N-terminus, which is cleaved off after the translocation through the ER (endoplasmic reticulum) membrane. Some N-terminal signal sequences are not cleaved off, remaining as transmembrane segments, but it does not mean these proteins are retained in the ER; they can be further sorted and included in vesicles. Non-receptor proteins generally function to transmit signals within the cell, either by providing sites for protein:protein interactions or by having some catalytic activity (contained within a catalytic domain), often both. Methods of predicting the existence of these various domains are well known in the art. Protein:protein interaction domains can be identified by comparison to other proteins. The SH2 domain, for example is a protein domain of about 100 amino acids first identified as a conserved sequence region between the proteins Src and Fps (Sadowski, et al., *Mol. Cell. Bio.* 6:4396, 1986). Similar sequences were later found in many other intracellular signal-transducing proteins. SH2 domains function as regulatory modules of intracellular signaling cascades by interacting with high affinity to phosphotyrosine-containing proteins in a sequence specific and strictly phosphorylation-dependent manner (Mayer and Baltimore, *Trends Cell. Biol.* 3:8, 1993). Kinase or phosphatase catalytic domains can be identified by comparison to other known catalytic domains with kinase or phosphatase activity. See, for example Hanks and Hunter, *FASEB J.* 9:576–595, 1995.

Primary sequence analysis of the PTP05 amino acid sequence (shown in SEQ ID NO:5 with isoforms shown in SEQ ID NO:6 and SEQ ID NO:7) reveals that it and its isoforms do not contain a signal sequence or transmembrane domain, and it is, therefore, an intracellular protein. Comparison to known protein sequences revels that PTP05 is comprised of several unique domains. These include a 187 amino acid N-terminal domain (shown from amino acid number 1–187 of SEQ ID NO:5), a 242 amino acid catalytic domain (shown from amino acid number 188–420 of SEQ ID NO:5), and a 5 amino acid C-terminal domain (shown from amino acid number 421–426 of SEQ ID NO:5).

Two additional isoforms of PTP05 were also identified, a "long" form (SEQ ID NO:6) and a "C-trunc" form (SEQ ID NO:7). The "long" form has a 37 amino acid insertion in the N-terminal domain (amino acids 44–80 of SEQ ID NO:6) which extends this domain to 224 amino acids. The catalytic domain extends from amino acid 225–457 of SEQ ID NO:6 and the C-terminal domain extents from amino acids 458–463 of SEQ ID NO:6. The "C-trunc" form results from a deletion of nucleotides 1415–1507 of SEQ ID NO:1, most likely due to alternative exon splicing. This deletion results in a replacement of the C-terminal 21 amino acids with a unique 7 amino acid sequence. This change eliminates a conserved C-terminal portion of the catalytic domain, which may affect enzymatic activity. The N-terminal domain of the "C-trunc" form extends from amino acid 1–87 of SEQ ID NO:7, the catalytic domain from amino acids 188–405 of SEQ ID NO:7 and the unique C-terminal domain from 406–412 of SEQ ID NO:7.

The domains of these proteins have a variety of uses. An example of such a use is to make a polypeptide consisting of a PTP05 catalytic domain and a heterologous protein such as glutathione S-transferase (GST). Such a polypeptide can be used in a biochemical assay for PTP05 catalytic activity useful for studying PTP05 substrate specificity or for identifying substances that can modulate PTP05 catalytic activity. Alternatively, one skilled in the art could create a PTP05 polypeptide lacking at least one of the three major domains. Such a polypeptide, when expressed in a cell, is able to form complexes with the natural binding partner(s) of PTP05 but unable to transmit any signal further downstream into the cell, ie. it would be signaling incompetent and thus would be useful for studying the biological relevance of PTP05 activity. (See, as an example, Gishizky, et al., PNAS:10889, 1995).

VI. An Antibody having Binding Affinity to a PTP05 Polypeptide an Antibody having Binding Affinity to a PTP10 Polypeptide and Hybridomas Producing these Antibodies The present invention also relates to antibodies having specific binding affinity to a PTP05 polypeptide or to a PTP10 polypeptide. The polypeptide may have the amino acid sequence set forth in SEQ ID NO:5, SEQ ID NO:6, SEQ ID NO:7, SEQ ID NO:8, or be a fragment thereof, or at least 6 contiguous amino acids thereof. Such an antibody may be identified by comparing its binding affinity to the desired polypeptide, for example a PTP05 polypeptide, with its binding affinity to another (non-PTP05) polypeptide. Those which bind selectively to the desired polypeptide would be chosen for use in methods requiring a distinction between the desired polypeptide and other polypeptides. Such methods could include, but should not be limited to, the analysis of altered expression of the desired polypeptide in tissue containing other polypeptides and assay systems using whole cells.

A PTP05 polypeptide or PTP10 polypeptide of the present invention can be used to produce antibodies or hybridomas. One skilled in the art will recognize that if an antibody is desired, such a peptide would be generated as described herein and used as an immunogen. Preferred PTP05 or PTP10 peptides in this respect are shown in the Examples section below. The antibodies of the present invention include monoclonal and polyclonal antibodies, as well as fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., *J. Immunol. Methods* 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or b-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz, et al., *Exp. Cell Res.* 175:109–124, 1988). Hybridomas secreting the desired antibodies are cloned and the class and subclass is determined using procedures known in the art (Campbell, "Monoclonal Antibody Technology: Laboratory Techniques in Biochemistry and Molecular Biology", supra, 1984).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger, et al., *J. Histochem. Cytochem.* 18:315, 1970; Bayer, et al., *Meth. Enzym.* 62:308, 1979; Engval, et al., *Immunot.* 109:129, 1972; Goding, *J. Immunol. Meth.* 13:215, 1976). The labeled antibodies of the present invention can be used for in vitro, in vivo, and in in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., Meth. Enzym. 34, Academic Press, N.Y., 1974). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, NY, pp. 289–307 (1992), and Kaspczak et al., Biochemistry 28:9230–8(1989).

VII. An Antibody Based Method and Kit for Detecting PTP05 or PTP10

The present invention encompasses a method of detecting a PTP05 polypeptide or a PTP10 polypeptide in a sample comprising incubating a test sample with one or more of the antibodies of the present invention and determining whether the antibody binds to the test sample. The method can include the steps of, for example: (a) contacting the sample with an above-described antibody, under conditions such that immunocomplexes form, and (b) detecting the presence of said antibody bound to the polypeptide. Altered levels, either an increase or decrease, of PTP05 or PTP10 in a sample as compared to normal levels may indicate an abnormality or disorder.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is compatible with the system utilized.

A kit contains all the necessary reagents to carry out the previously described methods of detection. The kit may comprise: (i) a first container containing an above-described antibody, and (ii) second container containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will recognize that the antibodies described in the present invention can readily be incorporated into one of the established kit formats which are well known in the art.

VIII. Isolation of Natural Binding Partners of PTP05 or PTP10

The present invention also relates to methods of detecting natural binding partners capable of binding to a PTP05 polypeptide or to a PTP10 polypeptide. A natural binding partner of PTP05 or PTP10 may be, for example, a substrate protein which is dephosphorylated as part of a signaling cascade. The binding partner(s) may be present within a complex mixture, for example, serum, body fluids, or cell extracts.

In general, methods for identifying natural binding partners comprise incubating a substance with a first polypeptide, PTP05 or PTP10 for the invention described herein, and detecting the presence of a substance bound to the first polypeptide. Preferred methods include the two-hybrid system of Fields and Song (supra) and co-immunoprecipitation wherein the first polypeptide is allowed to bind to a natural binding partner, then the polypeptide complex is immunoprecipitated using antibodies specific for the first polypeptide. The natural binding partner can then be isolated and identified by techniques well known in the art.

IX. Identification of and Uses for Substances Capable of Modulating PTP05 or PTP10 Activity The present invention also relates to a method of detecting a substance capable of modulating PTP05 or PTP10 activity. Such substances can either enhance activity (agonists) or inhibit activity (antagonists). Agonists and antagonists can be peptides, antibodies, products from natural sources such as fungal or plant extracts or small molecular weight organic compounds. In general, small molecular weight organic compounds are preferred. Examples of classes of compounds that can be tested for PTP05 or PTP10 modulating activity are, for example but not limited to, thiazoles (see for example co-pending U.S. applications 60/033,522 filed Dec. 19, 1996, Ser. No. 08/660,900 filed Jun. 7, 1996), and naphthopyrones (U.S. Pat. No. 5,602,171, issued Feb. 11, 1997).

In general the method comprises incubating cells that produce PTP05 or PTP10 in the presence of a test substance and detecting changes in the level of PTP05 or PTP10 activity or PTP05 or PTP10 binding partner activity. A change in activity may be manifested by increased or decreased phosphorylation of a PTP05 or PTP10 polypeptide, increased or decreased phosphorylation of a PTP05 or PTP10 substrate, increased or decreased binding to a PTP05 or PTP10 natural binding partner or increased or decreased biological response in cells. A method for detecting modulation of PTP05 or PTP10 activity using the phosphorylation of an artificial substrate is shown in the examples below. Biological responses can include, for example, proliferation, differentiation, survival, or motility. The substance thus identified would produce a change in activity indicative of the agonist or antagonist nature of the substance. Once the substance is identified it can be isolated using techniques well known in the art, if not already available in a purified form.

The present invention also encompasses a method of agonizing (stimulating) or antagonizing PTP05 or PTP10 associated activity in a mammal comprising administering to said mammal an agonist or antagonist to PTP05 or PTP10 in an amount sufficient to effect said agonism or antagonism. Also encompassed in the present application is a method of treating diseases in a mammal with an agonist or antagonist of PTP05- or PTP10-related activity comprising administering the agonist or antagonist to a mammal in an amount sufficient to agonize or antagonize PTP05 or PTP10 associated function(s). The particular compound can be administered to a patient either by itself or in a pharmaceutical composition where it is mixed with suitable carriers or excipient(s). In treating a patient, a therapeutically effective dose of the compound is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals. Cell culture assays and animal studies can be used for determining the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays by determining an $IC_{50}$ (i.e., the concentration of the test compound which achieves a half-maximal disruption of the protein complex, or a half-maximal inhibition of the cellular level and/or activity of a cellular component, ex. PTP05). A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated. Particular formulations suitable for parenteral administration of hydrophobic compounds can be found in U.S. Pat. No. 5,610,173, issued Mar. 11, 1997 and U.S. Provisional Application Ser. No. 60/039,870, filed Mar. 5, 1997, both of which are incorporated by reference herein in their entirety.

Agents intended to be administered intra cellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Small organic molecules may be directly administered intra cellularly due to their hydrophobicity.

Pharmaceutical compositions suitable for use in the present invention include compositions wherein the active ingredients are contained in an amount effective to achieve its intended purpose. Determination of an effective amount is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

X. Transgenic Animals

Also contemplated by the invention are transgenic animals useful for the study of PTP05 or PTP10 activity in complex in vivo systems. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human PTP05 or PTP10 polypeptide. Native expression in an animal may alternatively be reduced by providing an amount of antisense RNA or DNA effective to reduce expression of the target gene.

A variety of methods are available for the production of transgenic animals associated with this invention. DNA sequences encoding PTP05 or PTP10 can be injected into the pronucleus of a fertilized egg before fusion of the male and female pronuclei, or injected into the nucleus of an embryonic cell (e.g., the nucleus of a two-cell embryo) following the initiation of cell division (Brinster, et al., *Proc. Nat. Acad. Sci. USA* 82:4438, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for micro injection of DNA into the pronucleus of the zygote are well known to those of ordinary skill in the art (Hogan, et al., supra). Micro injection procedures for fish, amphibian eggs and birds are detailed in Houdebine and Chourrout, *Experientia* 47: 897–905, 1991). Other procedures for introduction of DNA into tissues of animals are described in U.S. Pat. No. , 4,945,050 (Sandford et al., Jul. 30, 1990).

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., Cell 63:1099–1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. (See, for example, Teratocarcinomas and Embryonic Stem Cells, A Practical Approach, E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra). DNA molecules introduced into ES cells can also be integrated into the chromosome through the process of homologous recombination. (See Capecchi, Science 244: 1288, 1989.) Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., Nature 338: 153, 1989), the teachings of which are incorporated by reference herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. (See Houdebine and Chourrout, supra; Pursel, et al., Science 244:1281, 1989; Simms, et al., Bio/Technology 6:179, 1988.)

Thus, the invention provides transgenic, nonhuman mammals containing a transgene encoding a PTP05 polypeptide or a PTP10 polypeptide or a gene effecting the expression of a PTP05 polypeptide or a PTP10 polypeptide. Such transgenic nonhuman mammals are particularly useful as an in vivo test system for studying the effects of introducing a PTP05 polypeptide or a PTP10 polypeptide, or for regulating the expression of a PTP05 polypeptide or a PTP10 polypeptide (i.e., through the introduction of additional genes, antisense nucleic acids, or ribozymes).

XI. Gene Therapy

PTP05 and/or PTP10 nucleic acid sequences, both mutated and non-mutated, will also be useful in gene therapy (reviewed in Miller, Nature 357:455–460, (1992). Miller states that advances have resulted in practical approaches to human gene therapy that have demonstrated positive initial results. The basic science of gene therapy is described in Mulligan, Science 260:926, 1993). As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In one preferred embodiment, an expression vector containing a PTP05 coding sequence, a PTP05 mutant coding sequence, a PTP10 coding sequence or a PTP10 mutant coding sequence, as described above, is inserted into cells, the cells are grown in vitro and then infused in large numbers into patients. In another preferred embodiment, a DNA segment containing a promoter of choice (for example a strong promoter) is transferred into cells containing an endogenous PTP05 or PTP10 in such a manner that the promoter segment enhances expression of the endogenous PTP05 gene (or PTP10) (for example, the promoter segment is transferred to the cell such that it becomes directly linked to the endogenous PTP gene).

The gene therapy may involve the use of an adenovirus containing PTP05 or PTP10 cDNA targeted to an appropriate cell type, systemic PTP05 or PTP10 increase by implantation of engineered cells, injection with PTP05 or PTP10 virus, or injection of naked PTP05 or PTP10 DNA into appropriate cells or tissues, for example adipose tissue.

Expression vectors derived from viruses such as retroviruses, vaccinia virus, adenovirus, adeno-associated virus, herpes viruses, other RNA viruses, or bovine papilloma virus, may be used for delivery of nucleotide sequences (e.g., cDNA) encoding recombinant PTP05 or PTP10 protein into the targeted cell population (e.g., tumor cells or fat cells). Methods which are well known to those skilled in the art can be used to construct recombinant viral vectors containing coding sequences. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., Nature 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of micro injection. (Capecchi MR, Cell 22:479–88, 1980). Once recombinant genes are introduced into a cell, they can be recognized by the cell's normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, Mol. Cell Biol. 7:2745–52, 1987); electroporation, wherein cells are exposed to large voltage pulses to introduce holes into the membrane (Chu G., et al., Nucleic Acids Res., 15:1311–26, 1987); lipofection/liposome fusion, wherein DNA is packaged into lipophilic vesicles which fuse with a target cell (Felgner PL., et al., Proc. Natl. Acad. Sci. USA. 84:7413–7, 1987); and particle bombardment using DNA bound to small projectiles (Yang NS. et al., Proc. Natl. Acad. Sci. 87:9568–72, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. (Curiel, et al., *Am. J. Respir. Cell. Mol. Biol.*, 6:247–52, 1992).

As used herein "gene transfer" means the process of introducing a foreign nucleic acid molecule into a cell. Gene transfer is commonly performed to enable the expression of a particular product encoded by the gene. The product may include a protein, polypeptide, antisense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

In another preferred embodiment, a vector having nucleic acid sequences encoding a PTP05 or PTP10 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a PTP05 or PTP10 nucleic acid is used in gene replacement. "Gene replacement" as used herein means supplying a nucleic acid sequence which is capable of being expressed in vivo in an animal and thereby providing or augmenting the function of an endogenous gene which is missing or defective in the animal. Methods of introducing the nucleic acid into the animal to be treated are as described above.

XII. Compounds that Modulate the Function of PTP05 or PTP10 Proteins

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al). The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules. WO 96/22976, published Aug. 1, 1996 by Ballinari et al. describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. U.S. patent application Ser. No. 08/702,232, filed Aug. 23, 1996, entitled "Indolinone Combinatorial Libraries and Related Products and Methods for the Treatment of Disease" by Tang et al. and Ser. No. 08/485,323, filed Jun. 7, 1995, entitled "Benzylidene-Z-Indoline Compounds for the Treatment of Disease" by Tang et al. and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. Application Ser. No. 08/702,232, filed Aug. 23, 1996, entitled "Indolinone Combinatorial Libraries and Related Products and Methods for the Treatment of Disease" by Tang et al., Ser. No. 08/485,323, filed Jun. 7, 1995, entitled "Benzylidene-Z-Indoline Compounds for the Treatment of Disease" by Tang et al., and WO 96/22976, published Aug. 1, 1996 by Ballinari et al. teach methods of indolinone synthesis, methods of testing the biological activity of indolinone compounds in cells, and inhibition patterns of indolinone derivatives.

Other examples of substances capable of modulating PTP05 or PTP10 activity include, but are not limited to, tyrphostins, quinazolines, quinoxolines, and quinolines.

The quinazolines, tyrphostins, quinolines, and quinoxolines referred to above include well known compounds such as those described in the literature. For example, representative publications describing quinazoline include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5,316,553; Kreighbaum and Corner, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43: 1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, Synthesis 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.*

37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc. pp.* 6363–6143:C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., "*J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992;; Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

Other compounds that could be used as modulators include oxindolinones such as those described in U.S. patent application Ser. No. 08/702,232 filed Aug. 23, 1996, incorporated herein by reference in its entirety, including any drawings.

EXAMPLES

Example 1

Isolation of cDNA Clones Encoding PTP05 and PTP10

The example below describes the isolation and identification of new PTP sequences from primary murine fat and rat basal forebrain and the subsequent cloning of a full-length PTP05 sequence Also described are probes useful for the detection of PTP05 and/or PTP10 in cells or tissues.

Materials and Methods:

Total RNAs were isolated using the Guanidine Salts/ Phenol extraction protocol of Chomczynski and Sacchi (P. Chomczynski and N. Sacchi, *Anal. Biochem.* 162, 156 (1987) from ob/ob mouse fat and, separately, rat basal forebrain. These RNAs were used to generate single-stranded cDNA using the Superscript Preamplification System (GIBCO BRL, Gaithersburg, Md.; Gerard, et al, *FOCUS* 11:66, 1989) under conditions recommended by the manufacturer. A typical reaction used 10 µg total RNA with 1.5 µg oligo(dT)$_{12-18}$ in a reaction volume of 60 µL. The product was treated with RNaseH and diluted to 100 µL with H$_2$O. For subsequent PCR amplification, 1–4 µL of this sscDNA was used in each reaction.

Degenerate oligonucleotides were synthesized on an Applied Biosystems 394 DNA synthesizer using established phosphoramidite chemistry, precipitated with ethanol and used unpurified for PCR. The sequence of the degenerate oligonucleotide primers follows:

```
                                        (SEQ ID NO:9)
PTPDFW = 5'-GAYTTYTGGVRNATGRTNTGGGA- (sense)

and
                                        (SEQ ID NO:10)
PTPHCSA = 5'-CGGCCSAYNCCNGCNSWRCARTG -3'
(antisense).
```

These primers were derived from the peptide sequences DFWXMXW(E/D) (SEQ ID NO:11) (sense strand from PTP catalytic domain) and HCXAGXG (SEQ ID NO:12) (antisense strand from PTP catalytic domain), respectively. The standard UIPAC designations for degenerate residue designations are: N=A, C, G, or T; R=A or G; Y=C or T; V=A, C or G; W=C or T; S=C or G; M=A or C; and H=A, C or T.

PCR reactions were performed using degenerate primers applied to the single-stranded cDNA listed above. The primers were added at a final concentration of 5 µM each to a mixture containing 10 mM Tris.HCl (pH 8.3), 50 mM KCl, 1.5 mM MgCl$_2$, 200 µM each deoxynucleoside triphosphate, 0.001% gelatin, 1.5 U AmpliTaq DNA Polymerase (Perkin-Elmer/Cetus), and 1–4 µL cDNA. Following 3 min denaturation at 95° C., the cycling conditions were 94° C. for 30 sec, 50° C. for 1 min, and 72° C. for 1 min 45 sec for 35 cycles. PCR fragments migrating between 350–400 bp were isolated from 2% agarose gels using the GeneClean Kit (Bio101), and T-A cloned into the pCR11 vector (Invitrogen Corp. U.S.A.) according to the manufacturer's protocol.

Colonies were selected for mini-plasmid DNA-preparations using Qiagen columns and the plasmid DNA was sequenced using cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul, S. F. et al., *J. Mol. Biol.* 215:403–10). Several copies of a clone encoding a novel PTP (R90-2-22), designated SuPTP05, was isolated from murine adipose tissue. A related clone, PTP10, was isolated from rat basal forebrain.

To obtain full-length cDNA encoding the novel phosphatase PTP05, RACE (rapid amplification of cDNA ends) was performed with sense or anti-sense oligonucleoides derived from the original PCR fragments. Marathon-Ready cDNA (Clontech, Palo Alto, Calif.) made from mouse testis was used in the RACE reactions with the following primers:

```
RACE primers:
                                         (SEQ ID NO:13)
5'-CACCGTTCGAGTATTTCAGATTGTGAAGAAGTCC-3'  (6595), (SEQ ID NO:14)
5'-GGACTTCTTCACAATCTGAAATACTCGAACGGTG-3'  (6596), (SEQ ID NO:15)
5'-CCGTTATGTGAGGAAGAGCCACATTACAGGACC-3'   (6599), (SEQ ID NO:16)
5'-GGTCCTGTAATGTGGCTCTTCCTCACATAACGG-3'   (6600),
AP-1, and AP-2 (Clontech).

RT-PCR primers for PTP05 sequencing:
                                         (SEQ ID NO:17)
5'-CACCGTTCGAGTATTTCAGATTGTGAAGAAGTCC-3'  (6595), (SEQ ID NO:18)
5'-GGTCCTGTAATGTGGCTCTTCCTCACATAACGG-3'   (6600).
```

Isolated cDNA fragments encoding SuPTP05 were confirmed by DNA sequencing and subsequently used as probes for the screening of a murine testis cDNA library.

Two murine testis cDNA libraries (lZapII, Stratagene, La Jolla, Calif. and lgt10, Clontech), were screened to isolate full-length transcripts encoding PTP05. The 5' or 3'-RACE fragments were $^{32}$P-labeled by random priming and used as hybridization probes at $2\times10^6$ cpm/mL following standard techniques for library screening. Pre-hybridization (3 hrs) and hybridization (overnight) were conducted at 42° C. in 5×SSC, 5× Denhart's solution, 2.5% dextran sulfate, 50 mM Na$_2$PO$_4$/NaHPO4 [pH 7.0], 50% formamide with 100 mg/mL denatured salmon sperm DNA. Stringent washes were performed at 65° C. in 0.1×SSC and 0.1% SDS. Several overlapping clones were isolated and found to span the collective sequences of the PCR fragment (R90-2-22) and the RACE products. The final sequence was verified by sequencing of both strains using a cycle sequencing dye-terminator kit with AmpliTaq DNA Polymerase, FS (ABI, Foster City, Calif.). Sequencing reaction products were run on an ABI Prism 377 DNA Sequencer. A full-length PTP10 clone can be obtained using the same techniques.

Results:

The primary murine PTP05 transcript is 1785 nucleotides and encodes a predicted polypeptide of 426 amino acids with a predicted molecular weight of 49122 daltons (SEQ ID NO:1 and SEQ ID NO:5). The PTP05 coding sequence is flanked by a 198 nucleotide 5'-untranslated region and a 279 nucleotide 3'-untranslated region ending with a poly(A) tail. There are inframe stop codons in all three frames upstream of the primary open reading frame. The ATG beginning at nucleotide position 199 conforms to the Kozak consensus for an initiating methionine. One clone (#6.1) contains an insertion of 111 bp at nucleotide 328 resulting in an addition 37 amino acids added inframe to the coding sequence. A second clone (#10.1) has a deletion of 93 bp beginning at nucleotide 1415, resulting in a frame-shift and premature termination. Upstream of the 198 bp 5'UTR, the numerous clones diverge into 2 groups, extending the 5'UTR an additional 98–153 bp. Furthermore, one clone (#15.3) lacks the polyA tail at nucleotide 1758 extends the 3' UTR by another 300 nucleotides.

The amino acid sequence shows no signal sequence or a transmembrane domain, and PTP05 is therefore predicted to be an intracellular protein. The N-terminal domain of murine PTP05 extends from amino acid 1 to 187 and is unique, ie. contains no significant homology to any protein in the non-redundant protein database. The non-redundant protein database consists of peptide sequences from GenBank Genpept, PIR, and SwissProt. There is a single protein tyrosine phosphatase catalytic domain extending from amino acids 188–420. The catalytic domain shares a relatively low level of identity at the amino acid level (40–47%) to PTPs from 5 distinct families: ZPEP (mouse) (46.7%), PTP-BAS (human) (45.6%), DEP (human) (40.5%), PTP-g (human) (40.6%), suggesting that it represents a new family of PTPs. The C-terminal tail of PTP05 extends beyond the catalytic domain from amino acids 421–426 and is not homologous to other protein tyrosine phosphatases. Motifs found in the cytoplasmic domain of other mammalian PTPs that are absent from PTP05 include: SH2, Talin/Ezrin-like, PEST, GLGF, and Retinaldehyde-binding protein domains. Owing to its divergent catalytic domain and absence of well-known non-catalytic motifs, we have designated PTP05 as a new and distinct family of protein tyrosine phosphatases.

An alternative form of murine PTP05 contains an insertion of 111-bp in the N-terminal coding region, extending the sequence by 37 a (SEQ ID NO:2 and SEQ ID NO:6). This 1,896 bp "long" form of murine PTP05 encodes a polypeptide of 463 amino acids with a predicted molecular weight of 53716 daltons. The insertion is located at amino acid positions 44–80 and is not significantly homologous to other proteins in the non-redundant protein database.

A third form of PTP05 has a deletion of nucleotides 1415–1507 resulting in a frame shift and C-terminal truncation leading to an alternate sequence from amino acids 406–412 (SEQ ID NO:3 and SEQ ID NO:7). The 1,692 bp "C-trunc" murine PTP05 encodes a polypeptide of 412 amino acids with a predicted molecular weight of 47233 daltons.

The rat PTP10 clone shares 92% identity at the DNA level (320 nucleotides) and 85% amino acid identity at the protein level (107 amino acids) with murine PTP05 (See FIG. 1). The level of homology of the two catalytic domains suggests that PTP05 and PTP10 are distinct but related genes, and thus PTP10 is considered to be a second member of this new PTP family. Partial sequences of rat PTP10 are shown in SEQ ID NO:4 (nucleic acid) and SEQ ID NO:8 (amino acid).

Example 2

Expression of PTP05

The example below shows the evaluation of PTP05 and PtP10 expression in normal murine tissues. A similar analysis can be done in human tissues using a human PTP05 or PTP10.

Materials and Methods:

A mouse normal tissue Northern blot containing 2 µg polyA+ mRNA per lane from 8 different mouse adult tissues (lung, testis, brain, heart, liver, kidney, spleen, skeletal muscle) on a charge-modified nylon membrane was obtained from Clontech (#7762-1, Palo Alto, Calif.).

The membrane was hybridized with randomly primed [a$^{32}$P]dCTP-labeled probe synthesized from a 241 bp EcoRI fragment of R90-2-22 (see above). Hybridization was performed at 42° C. overnight in 5×SSC, 2% SDS, 10× Denhardt's solution, 50% formamide, 100 µg/mL denatured salmon sperm DNA with 1–2×10$^6$ cpm/mL of $^{32}$P-labeled DNA probe. The membrane was washed at room temperature in 2×SSC/0.05% SDS for 30 min and followed by 50° C. in 0.2×SSC/0.1% SDS for 30 min, and exposed overnight on Kodak XAR-2 film.

A similar analysis was performed using the 320 bp rat PTP10 fragment as a probe of a rat normal tissue Northern blot.

RT-PCR Detection of Novel PTPs

Total RNA was isolated from fresh frozen mouse or rat (separately) tissues by centrifugation through a cesium chloride cushion. Twenty µg of total RNA was reverse transcribed with random hexamers and Moloney murine leukemia virus reverse transcriptase (Super-ScriptII, GIBCO BRL, Gaithersburg, Md.). PCR was then used to amplify cDNA encoding SuPTP05. RT-PCR reactions lacking only the reverse transcriptase were performed as controls. PCR products were electrophoresed on 3% agarose gels, visualized by ethidium bromide staining and photographed on a UV light box. The intensity for a 161-bp fragment specific to murine PTP05 were compared among different RNA samples. A rating of 3 represents large quantities of PTP05 transcript identified by Northern blot analysis while a rating of 0 represents little or none of the transcript was detected.

Results:

By Northern analysis, a single murine PTP05 mRNA transcript of approximately 3.4 kb was identified, and found to be exclusively expressed in the testis. The lung, brain, heart, liver, kidney, spleen, skeletal muscle samples were negative. PTP10 hybridized to a slightly smaller band and was also found only in the testis in this analysis. Northern analysis identified two rat PTP10 mRNA transcripts of approximately 3.3 kb and 1.8 kb, exclusively expressed in the testis. The rat heart, brain, spleen, lung, liver, skeletal muscle, and kidney samples were negative.

RT-PCR with gene specific primer-pairs showed that expression of the transcripts encoding PTP05 confirmed the results from Northern analysis and also detected low levels in adipose, kidney, small intestine, and cells/tissues of hematopoietic or immune origin including spleen, thymus, lymph node, bone marrow, and peripheral blood lymphocytes). RT-PCR with rat PTP10 gene specific primers confirmed the results from the Northern analysis, detecting a strong signal only in rat testis sscDNA and not in templates corresponding to rat skeletal muscle, heart, kidney, spleen, adrenal gland, lung, liver, intestine, uterus, spinal cord, brain, cortex and ovary.

The relatively small selective expression of PTP05 in cells of hematopoietic or immune origin suggests a potential involvement in immune regulation including T and B cell survival, differentiation or co-stimulation, and/or inflammatory, immunosuppressive or autoimmune disorders. Additionally, expression in adipose tissue (also the source from which PTP05 was originally isolated) suggests a possible role in metabolic disorders such as diabetes.

Example 3

Recombinant Expression of PTP05

The following example illustrates the construction of vectors for expression of recombinant PTP05 and the creation of recombinant cell lines expressing PTP05. Similar vectors and recombinant cell lines can be generated using PTP10 and the techniques described herein.

Contruction of Expression Vectors

Expression constructs were generated by PCR-assisted mutagenesis in which the entire coding domain of PTP05 was tagged on its carboxy-terminal end with the hemophilus influenza hemaglutinin (HA) epitope YPYDVPDYAS (SEQ ID NO:19) (Pati, supra). This construct was introduced into two mammalian expression vectors: PLXSN (Miller, A. D. & Rosman, G. J., *Biotechniques* 7, 980–988, 1989) for the generation of virus producing lines; and PRK5 for transient expression in mammalian cells.

Dominant negative PTP05 constructs were also made in both pLXSN and pRK5 by mutation of the invariant Cys in the conserved His-Cys-Ser-Ala-Gly motif (SEQ ID NO:20) to an Ala by PCR mutagenesis.

The entire PTP05 open reading frame excluding the initiating methionines was generated by PCR and ligated into pGEX vector for bacterial production of GST-fusion proteins for immunization of rabbits for antibody production. This vector contains the glutathione-S-transferase coding sequence followed by a polylinker for generating recombinant fusion proteins. The GST moiety comprises the N-terminal portion of the fusion protein.

Transient Expression in Mammalian Cells

The PRK5 expression plasmids (10 μg DNA/100 mm plate) containing the HA-tagged PTP05 gene can be introduced into COS and 293 cells with lipofectamine (Gibco BRL). After 72 hours, the cells were harvested in 0.5 mL solubilization buffer (20 mM HEPES pH7.35, 150 mM NaCl, 10% glycerol, 1% Triton X-100, 1.5 mM MgCl$_2$, 1 mM EGTA, 2 mM phenylmethylsulfonyl fluoride, 1 μg/ml aprotinin). Sample aliquots were resolved by SDS polyacrylamide gel electrophoresis (PAGE) on 15% acrylamide/0.5% bis-acrylamide gels and electrophoretically transferred to nitrocellulose. Non-specific binding was blocked by pre-incubating blots in Blotto (phosphate buffered saline containing 5% w/v non-fat dried milk and 0.2% v/v nonidet P-40 (Sigma)), and recombinant protein was detected using a murine Mab to the HA decapeptide tag. Alternatively, recombinant protein can be detected using various PTP05-specific antisera.

Generation of Virus Producing Cell Lines pLXSN recombinant constructs containing the PTP05 gene were transfected into an amphotropic helper cell line PA317 using CaCl$_2$ mediated transfection. After selection on G418, the cells were plated on normal media without G418 (500 μg/mL). Supernatants from resistant cells were used to infect the ecotropic helper cell line GP+E86, and cells again selected on G418. Resistant cells were again taken off G418, and the supernatants harvested every 8–12 hours and pooled as virus stock. Redemann et al., 1992, *Mol. Cell. Biol.* 12: 491–498. Viral stock titers were typically ~$10^6$/mL.

Stable Expression in Mammalian Cells

NIH-3T3, and BALB/3T3 cells were grown in 100 mm plates with DMEM (Gibco) containing 10% fetal calf serum (FCS). The cells were superinfected with the PTP05 retrovirus by adding approximately 3 mL viral supernatant to 15 mL culture media for approximately 24 hours. Cells expressing the retroviral constructs were then selected by growth in DMEM/10% FCS supplemented with 500 μg/mL G418.

Example 4

Generation of Anti-PTP05 Antibodies

PTP05-specific immunoreagents were raised in rabbits against a pool of three KLH-conjugated synthetic peptides corresponding to unique sequences present in human PTO05 or PTP10. The peptides (see below) were conjugated at the C-terminal residue with KLH.

Peptides Used for Immunizing Rabbits:

PTP05:

(SEQ ID NO:21)
peptide 433A - MSSPRKVRGKTGRDNDEEEGNSGNLNLRN (SEQ ID NO:22)
peptide 431A - SPVLSGSSRLSKDTETSVSEKELTQLAQI and (SEQ ID NO:23)
peptide 432A - WDVSDRSLRNRWNSMDSETAGPSKTVSPV.

Additional immunoreagents were generated by immunizing rabbits with a purified preparation of a GST-fusion protein containing the entire coding region of PTP05. The GST-fusion proteins were produced in DH5-alpha *E. coli* bacteria as described in Smith, et al Gene 67:31, 1988. Bacterial protein lysates were purified on glutathione-sepharose matrix as described in Smith, et al., supra.

Example 5

Assay for PTP05 Activity

Materials and Methods:

Recombinant wild-type and dominant negative (signaling incompetent) PTP05 (see Example 3, supra) were purified from bacteria as GST-fusion proteins. Lysates were bound to a glutathione-sepharose matrix and washed twice with 1×HNTG, followed by one wash with a buffer containing 100 mM 2-(N-morpholino)ethansulfonic acid (MES), pH 6.8, 150 mM NaCl, and 1 mM EDTA.

The assay for phosphatase activity was essentially done as described by Pei et al.(1993) using p-nitrophenolphosphate (PNPP) as a generic PTP substrate. Briefly, after the last washing step, reactions were started by adding 50 mL Assay Buffer (100 mM MES pH 6.8, 150 mM NaCl, 10 mM DTT, 2 mM EDTA, and 50 mM PNPP) to the matrix bound proteins. Samples were incubated for 20 min. at 23° C. The reactions were terminated by mixing 40 µL of each sample with 960 µL 1 N NaOH, and the absorbance of p-nitrophenol was determined at 450 nm. To control for the presence of PTP05 in the precipitates, the precipitates were boiled in SDS sample buffer and analyzed by SDS-PAGE. The presence of PTP05 was then detected by immunoblot analysis with anti-PTP05 antibodies.

Example 6

Screening Systems for the Identification of Inhibitors of PTP05 or PTP10 Activity Assays may be performed in vitro or in vivo and are described in detail herein or can be obtained by modifying existing assays, such as the growth assay described in patent application Ser. No. 08/487,088, filed Jun. 7, 1995, by Tang et al., and entitled "Novel Pharmaceutical Compounds," or the assays described in patent application Ser. No. 60/005,167, filed Oct. 13, 1995 by Seedorf et al., and entitled "Diagnosis and Treatment of TKA-1 Related Disorders," all of which are hereby incorporated herein by reference in their entirety including any drawings. Another assay which could be modified to use the genes of the present invention is described in International Application No. WO 94/23039, published Oct. 13, 1994, hereby incorporated herein by reference in its entirety including any drawings. Other possibilities include detecting kinase activity in an autophosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase (Fields and Song, U.S. Pat. No. 5,283,173, issued Feb. 1, 1994, incorporated by reference herein, including any drawings).

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

In view of the degeneracy of the genetic code, other combinations of nucleic acids also encode the claimed peptides and proteins of the invention. For example, all four nucleic acid sequences GCT, GCC, GCA, and GCG encode the amino acid alanine. Therefore, if for an amino acid there exists an average of three codons, a polypeptide of 100 amino acids in length will, on average, be encoded by $3^{100}$, or $5 \times 10^{47}$, nucleic acid sequences. Thus, a nucleic acid sequence can be modified to form a second nucleic acid sequence, encoding the same polypeptide as encoded by the first nucleic acid sequences, using routine procedures and without undue experimentation. Thus, all possible nucleic acids that encode the claimed peptides and proteins are also fully described herein, as if all were written out in full taking into account the codon usage, especially that preferred in humans. Furthermore, changes in the amino acid sequences of polypeptides, or in the corresponding nucleic acid sequence encoding such polypeptide, may be designed or selected to take place in an area of the sequence where the significant activity of the polypeptide remains unchanged. For example, an amino acid change may take place within a β-turn, away from the active site of the polypeptide. Also changes such as deletions (e.g. removal of a segment of the polypeptide, or in the corresponding nucleic acid sequence encoding such polypeptide, which does not affect the active site) and additions (e.g. addition of more amino acids to the polypeptide sequence without affecting the function of the active site, such as the formation of GST-fusion proteins, or additions in the corresponding nucleic acid sequence encoding such polypeptide without affecting the function of the active site) are also within the scope of the present invention. Such changes to the polypeptides can be performed by those with ordinary skill in the art using routine procedures and without undue experimentation. Thus, all possible nucleic and/or amino acid sequences that can readily be determined not to affect a significant activity of the peptide or protein of the invention are also fully described herein.

Other embodiments are within the following claims.

What is claimed is:

1. An isolated or purified polypeptide comprising an amino acid sequence having
   (a) the full length amino acid sequence set forth in SEQ BY NO:5, SEQ ID NO:6, or SEQ ID NO:7;
   (b) the full length amino acid sequence of the sequence set forth in SEQ ID NO:5, SEQ ID NO:6, or SEQ ID NO:7, except that it lacks one or more of the following segments of amino acid residues: 1–187 and 421–426 of SEQ ID NO:5, 44–80 and 458–463 of SEQ ID NO:6, or 1–87 and 406–412 of SEQ ID NO:7, wherein said polypeptide has tyrosine phosphatase activity;
   (c) the amino acid sequence set forth in SEQ ID NO:5, SEQ ID NO:6, or SEQ ID NO:7 from amino acid residues 188–420 of SEQ ID NO:5, 225–457 of SEQ ID NO:6, or 188–405 of SEQ ID NO:7, wherein said polypeptide has tyrosine phosphatase activity; or
   (d) the full length amino acid sequence set forth in SEQ ID NO:5, SEQ ID NO:6, or SEQ ID NO:7 except that it lacks one or more of the domains selected from the group consisting of an N-terminal domain and C-terminal domain, wherein said polypeptide has tyrosine phosphatase activity.

2. An isolated or purified polypeptide comprising an amino acid sequence having the full length amino acid sequence set forth in SEQ ID NO:5, SEQ ID NO:6, or SEQ ID NO:7.

3. The isolated or purified polypeptide of claim 2, except that it lacks one or more of the following segments of amino acid residues: 1–187 and 421–426 of SEQ ID NO:5, 44–80 and 458–463 of SEQ -ID NO:6, or 1–87 and 406–412 of SEQ ID NO:7, wherein said polypeptide has tyrosine phosphatase activity.

4. The isolated or purified polypeptide of claim 2, except that it lacks one or more of the domains selected from the group consisting of an N-terminal domain and C-terminal domain, wherein said polypeptide has tyrosine phosphatase activity.

5. An isolated or purified polypeptide comprising an amino acid sequence having from amino acid residues 188–420 of SEQ ID NO:5, 225–457 of SEQ ID NO:6, or 188–405 of SEQ ID NO:7, wherein said polypeptide has tyrosine phosphatase activity.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 1785 base pairs
      (B) TYPE: nucleic acid
      (C) STRANDEDNESS: single
      (D) TOPOLOGY: linear (xi) SEQUENCE DESCRIPTION: SEQ ID NO:1:

```
GGTTATGTCT GACTCACTGC ACTGGAGTTT GGCAAAAGCA TCTCAGAAGT GGTTGTGCTT     60
TTTTGAATGA AATGATCAAT GGAGTGCTCC AGTTGTATGC TGGCCTCTGG ATACTAACTA    120
GACCTGCCTG ACTCCAGGAA CTAAGGCTCA GTATCTGCAG AAGCTTTTTG CCCATCTCAT    180
TCCGGCTATG GGACAACAT GTCTTCACCC AGGAAGGTTA GAGGAAAAAC TGGAAGAGAT    240
AATGATGAAG AGGAGGGTAA TTCAGGTAAC CTGAATCTCC GCAACTCTTT GCCTTCATCG    300
AGTCAGAAAA TGACGCCTAC GAAGCCGATT TTTGGGAATA AAATGAATTC AGAGAATGTA    360
AAACCCTCCC ATCACCTGTC ATTCTCAGAT AAGTATGAGC TTGTTTACCC AGAGCCTTTG    420
GAAAGTGACA CTGATGAGAC TGTGTGGGAT GTCAGTGACC GGTCTCTCAG AAACAGGTGG    480
AACAGTATGG ATTCAGAGAC TGCAGGGCCG TCAAAGACTG TCTCCCCAGT GCTTTCTGGT    540
AGTAGTAGGC TCTCAAAGGA CACTGAAACA TCTGTCTCTG AAAAGGAGCT AACTCAGTTG    600
GCTCAGATTC GACCATTAAT ATTCAACAGT TCTGCACGGT CTGCTATGCG GGATTGTTTG    660
AACACGCTTC AGAAAAAAGA AGAACTTGAT ATCATCCGTG AGTTTTTGGA GTTAGAACAA    720
ATGACTCTGC CTGATGACTT CAATTCTGGG AATACACTAC AGAACAGAGA TAAGAACAGA    780
TACCGAGATA TTCTTCCATA TGATTCAACA CGTGTTCCTC TTGGAAAAAA CAAGGACTAC    840
ATCAACGCTA GTTATATTAG AATAGTAAAT CATGAAGAAG AGTATTTTTA TATTGCCACT    900
CAAGGACCAT TGCCAGAAAC TATAGAAGAC TTTTGGCAAA TGGTTCTGGA AAATAATTGT    960
AATGTTATTG CTATGATAAC CAGAGAGATA GAATGTGGAG TTATCAAGTG TTACAGTTAC   1020
TGGCCCATTT CTCTGAAGGA GCCTTTGGAA TTCGAACACT TTAGTGTCTT TCTGGAGACC   1080
TTTCATGTAA CTCAATATTT CACCGTTCGA GTATTTCAGA TTGTGAAGAA GTCCACAGGA   1140
AAGAGCCAAT GTGTAAAACA CTTGCAGTTC ACCAAGTGGC CAGACCATGG CACTCCTGCC   1200
TCAGCAGATT TTTTCATAAA ATATGTCCGT TATGTGAGGA AGAGCCACAT TACAGGACCC   1260
CTCCTTGTTC ACTGCAGTGC TGGTGTAGGC CGAACAGGGG TGTTCATATG TGTGGATGTT   1320
GTGTTCTCTG CCATCGAGAA GAACTACTCT TTTGACATTA TGAACATAGT GACCCAGATG   1380
AGAAAGCAGC GCTGTGGCAT GATTCAAACC AAGGAGCAGT ACCAGTTTTG TTATGAAATT   1440
GTGCTTGAAG TTCTTCAGAA CCTTCTGGCT TTGTATTAAG AGAGACTTCT GCGCCTGTCC   1500
CTCGAGGTTA CCGAGCAGCT TGGAGCCTGA GCCGTGCTGA AGCGTCTGCG GGCCGTGCAG   1560
TCTGCCTTCT GATTTTTCTC TCTGAAAGTC CCTGAAGGTA GCACTACTGG GCACAGAGTG   1620
AACTGTTTCC ACTTGATCTT TCTGAACAAG AGCAAAATAC CCTCCATGCC TTCTACGGAA   1680
ACGGAAGTTG CATGAAACAA CCTCCGCTTG GCTGTCTGGT TTGTGGTATT ACAGAGCTTA   1740
ATAAAAGACT TAGATGTGAA AAAAAAAAAA AAAAAAAAAA AAAAA               1785
```

(2) INFORMATION FOR SEQ ID NO:2:

(i) SEQUENCE CHARACTERISTICS:
        (A) LENGTH:        1896 base pairs
        (B) TYPE:          nucleic acid
        (C) STRANDEDNESS:  single
        (D) TOPOLOGY:     linear (xi) SEQUENCE DESCRIPTION: SEQ ID NO:2:

```
GGTTATGTCT GACTCACTGC ACTGGAGTTT GGCAAAAGCA TCTCAGAAGT GGTTGTGCTT      60

TTTTGAATGA AATGATCAAT GGAGTGCTCC AGTTGTATGC TGGCCTCTGG ATACTAACTA     120

GACCTGCCTG ACTCCAGGAA CTAAGGCTCA GTATCTGCAG AAGCTTTTTG CCCATCTCAT     180

TCCGGCTATG GGACAACAT GTCTTCACCC AGGAAGGTTA GAGGAAAAAC TGGAAGAGAT      240

AATGATGAAG AGGAGGGTAA TTCAGGTAAC CTGAATCTCC GCAACTCTTT GCCTTCATCG     300

AGTCAGAAAA TGACGCCTAC GAAGCCGGTA CAAAATAAAA ATCTCATGAA GTATGAAGAA     360

CACTTAGATA TATTGATGGT GTTTTTATTG ATAAAAACCA TATGGTATAA TGTCTTCAAA     420

TTATGGAAAG GCAAGCTTAT TTTTGGGAAT AAAATGAATT CAGAGAATGT AAAACCCTCC     480

CATCACCTGT CATTCTCAGA TAAGTATGAG CTTGTTTACC AGAGCCTTT GGAAAGTGAC      540

ACTGATGAGA CTGTGTGGGA TGTCAGTGAC CGGTCTCTCA GAAACAGGTG AACAGTATG      600

GATTCAGAGA CTGCAGGGCC GTCAAAGACT GTCTCCCCAG TGCTTTCTGG TAGTAGTAGG    660

CTCTCAAAGG ACACTGAAAC ATCTGTCTCT GAAAAGGAGC TAACTCAGTT GGCTCAGATT     720

CGACCATTAA TATTCAACAG TTCTGCACGG TCTGCTATGC GGGATTGTTT GAACACGCTT     780

CAGAAAAAAG AAGAACTTGA TATCATCCGT GAGTTTTTGG AGTTAGAACA AATGACTCTG     840

CCTGATGACT TCAATTCTGG GAATACACTA CAGAACAGAG ATAAGAACAG ATACCGAGAT     900

ATTCTTCCAT ATGATTCAAC ACGTGTTCCT CTTGGAAAAA ACAAGGACTA CATCAACGCT     960

AGTTATATTA GAATAGTAAA TCATGAAGAA GAGTATTTTT ATATTGCCAC TCAAGGACCA    1020

TTGCCAGAAA CTATAGAAGA CTTTTGGCAA ATGGTTCTGG AAAATAATTG TAATGTTATT    1080

GCTATGATAA CCAGAGAGAT AGAATGTGGA GTTATCAAGT GTTACAGTTA CTGGCCCATT    1140

TCTCTGAAGG AGCCTTTGGA ATTCGAACAC TTTAGTGTCT TTCTGGAGAC CTTTCATGTA    1200

ACTCAATATT TCACCGTTCG AGTATTTCAG ATTGTGAAGA AGTCCACAGG AAAGAGCCAA    1260

TGTGTAAAAC ACTTGCAGTT CACCAAGTGG CCAGACCATG GCACTCCTGC CTCAGCAGAT    1320

TTTTTCATAA AATATGTCCG TTATGTGAGG AAGAGCCACA TTACAGGACC CCTCCTTGTT    1380

CACTGCAGTG CTGGTGTAGG CCGAACAGGG GTGTTCATAT GTGTGGATGT TGTGTTCTCT    1440

GCCATCGAGA AGAACTACTC TTTTGACATT ATGAACATAG TGACCCAGAT GAGAAAGCAG    1500

CGCTGTGGCA TGATTCAAAC CAAGGAGCAG TACCAGTTTT GTTATGAAAT TGTGCTTGAA    1560

GTTCTTCAGA ACCTTCTGGC TTTGTATTAA GAGAGACTTC TGCGCCTGTC CCTCGAGGTT    1620

ACCGAGCAGC TTGGAGCCTG AGCCGTGCTG AAGCGTCTGC GGGCCGTGCA GTCTGCCTTC    1680

TGATTTTTCT CTCTGAAAGT CCCTGAAGGT AGCACTACTG GCACAGAGT GAACTGTTTC    1740

CACTTGATCT TTCTGAACAA GAGCAAAATA CCCTCCATGC CTTCTACGGA AACGGAAGTT    1800

GCATGAAACA ACCTCCGCTT GGCTGTCTGG TTTGTGGTAT TACAGAGCTT AATAAAAGAC    1860

TTAGATGTGA AAAAAAAAAA AAAAAAAAA AAAAAA                               1896
```

(2) INFORMATION FOR SEQ ID NO:3:

(i) SEQUENCE CHARACTERISTICS:
        (A) LENGTH:        1692 base pairs

```
        (B) TYPE:            nucleic acid
        (C) STRANDEDNESS:    single
        (D) TOPOLOGY:        linear (xi) SEQUENCE DESCRIPTION: SEQ ID NO:3:

GGTTATGTCT GACTCACTGC ACTGGAGTTT GGCAAAAGCA TCTCAGAAGT GGTTGTGCTT      60

TTTTGAATGA AATGATCAAT GGAGTGCTCC AGTTGTATGC TGGCCTCTGG ATACTAACTA     120

GACCTGCCTG ACTCCAGGAA CTAAGGCTCA GTATCTGCAG AAGCTTTTTG CCCATCTCAT     180

TCCGGCTATG GGACAACAT  GTCTTCACCC AGGAAGGTTA GAGGAAAAAC TGGAAGAGAT     240

AATGATGAAG AGGAGGGTAA TTCAGGTAAC CTGAATCTCC GCAACTCTTT GCCTTCATCG     300

AGTCAGAAAA TGACGCCTAC GAAGCCGATT TTTGGGAATA AAATGAATTC AGAGAATGTA     360

AAACCCTCCC ATCACCTGTC ATTCTCAGAT AAGTATGAGC TTGTTTACCC AGAGCCTTTG     420

GAAAGTGACA CTGATGAGAC TGTGTGGGAT GTCAGTGACC GGTCTCTCAG AAACAGGTGG     480

AACAGTATGG ATTCAGAGAC TGCAGGGCCG TCAAAGACTG TCTCCCCAGT GCTTTCTGGT     540

AGTAGTAGGC TCTCAAAGGA CACTGAAACA TCTGTCTCTG AAAAGGAGCT AACTCAGTTG     600

GCTCAGATTC GACCATTAAT ATTCAACAGT TCTGCACGGT CTGCTATGCG GGATTGTTTG     660

AACACGCTTC AGAAAAAAGA AGAACTTGAT ATCATCCGTG AGTTTTTGGA GTTAGAACAA     720

ATGACTCTGC CTGATGACTT CAATTCTGGG AATACACTAC AGAACAGAGA TAAGAACAGA     780

TACCGAGATA TTCTTCCATA TGATTCAACA CGTGTTCCTC TTGGAAAAAA CAAGGACTAC     840

ATCAACGCTA GTTATATTAG AATAGTAAAT CATGAAGAAG AGTATTTTTA TATTGCCACT     900

CAAGGACCAT TGCCAGAAAC TATAGAAGAC TTTTGGCAAA TGGTTCTGGA AAATAATTGT     960

AATGTTATTG CTATGATAAC CAGAGAGATA GAATGTGGAG TTATCAAGTG TTACAGTTAC    1020

TGGCCCATTT CTCTGAAGGA GCCTTTGGAA TTCGAACACT TTAGTGTCTT TCTGGAGACC    1080

TTTCATGTAA CTCAATATTT CACCGTTCGA GTATTTCAGA TTGTGAAGAA GTCACAGGA     1140

AAGAGCCAAT GTGTAAAACA CTTGCAGTTC ACCAAGTGGC CAGACCATGG CACTCCTGCC    1200

TCAGCAGATT TTTTCATAAA ATATGTCCGT TATGTGAGGA AGAGCCACAT TACAGGACCC    1260

CTCCTTGTTC ACTGCAGTGC TGGTGTAGGC CGAACAGGGG TGTTCATATG TGTGGATGTT    1320

GTGTTCTCTG CCATCGAGAA GAACTACTCT TTTGACATTA TGAACATAGT GACCCAGATG    1380

AGAAAGCAGC GCTGTGGCAT GATTCAAACC AAGGTTACCG AGCAGCTTGG AGCCTGAGCC    1440

GTGCTGAAGC GTCTGCGGGC CGTGCAGTCT GCCTTCTGAT TTTTCTCTCT GAAAGTCCCT    1500

GAAGGTAGCA CTACTGGGCA CAGAGTGAAC TGTTTCCACT TGATCTTTCT GAACAAGAGC    1560

AAAATACCCT CCATGCCTTC TACGGAAACG GAAGTTGCAT GAAACAACCT CCGCTTGGCT    1620

GTCTGGTTTG TGGTATTACA GAGCTTAATA AAAGACTTAG ATGTGAAAAA AAAAAAAAA    1680

AAAAAAAAA AA                                                         1692

(2) INFORMATION FOR SEQ ID NO:4:

(i) SEQUENCE CHARACTERISTICS:
         (A) LENGTH:         320 base pairs
         (B) TYPE:           nucleic acid
         (C) STRANDEDNESS:   single
         (D) TOPOLOGY:       linear (xi) SEQUENCE DESCRIPTION: SEQ ID NO:4:

GAAAATAATT GTAATGTTAT TGCTATGATA ACCAGAGAGA TAGAAGGTGG AGTTATCAAG      60

TGTTGCAGTT ACTGGCCCGT TTCTCTGAAG GAGCCTTTGG AATTCAAACA CTTTCATGTC     120
```

```
CTTCTGGAGA ACTTTCAGAT AACTCAGTAT TTTGTCATCC GAATATTTCA AATTGTGAAG      180

AAGTCCACAG GAAAGAGTCA CTCTGTAAAA CACTTGCAGT TCATCAAATG GCCAGACCAT      240

GGCACTCCTG CCTCAGTAGA TTTTTTCATC AAATATGTCC GTTATGTGAG GAAGAGCCAC      300

ATTACAGGAC CCCTCCTTGT                                                  320
```

(2) INFORMATION FOR SEQ ID NO:5:

(i) SEQUENCE CHARACTERISTICS:
        (A) LENGTH:      426 amino acids
        (B) TYPE:        amino acid
        (C) STRANDEDNESS:  single
        (D) TOPOLOGY:    linear (ii) MOLECULE TYPE:      peptide (xi) SEQUENCE DESCRIPTION: SEQ ID NO:5:

```
Met Ser Ser Pro Arg Lys Val Arg Gly Lys Thr Gly Arg Asp Asn Asp
 1               5                  10                  15

Glu Glu Glu Gly Asn Ser Gly Asn Leu Asn Leu Arg Asn Ser Leu Pro
             20                  25                  30

Ser Ser Ser Gln Lys Met Thr Pro Thr Lys Pro Ile Phe Gly Asn Lys
         35                  40                  45

Met Asn Ser Glu Asn Val Lys Pro Ser His His Leu Ser Phe Ser Asp
 50                  55                  60

Lys Tyr Glu Leu Val Tyr Pro Glu Pro Leu Glu Ser Asp Thr Asp Glu
65                  70                  75                  80

Thr Val Trp Asp Val Ser Asp Arg Ser Leu Arg Asn Arg Trp Asn Ser
                 85                  90                  95

Met Asp Ser Glu Thr Ala Gly Pro Ser Lys Thr Val Ser Pro Val Leu
            100                 105                 110

Ser Gly Ser Ser Arg Leu Ser Lys Asp Thr Glu Thr Ser Val Ser Glu
        115                 120                 125

Lys Glu Leu Thr Gln Leu Ala Gln Ile Arg Pro Leu Ile Phe Asn Ser
    130                 135                 140

Ser Ala Arg Ser Ala Met Arg Asp Cys Leu Asn Thr Leu Gln Lys Lys
145                 150                 155                 160

Glu Glu Leu Asp Ile Ile Arg Glu Phe Leu Glu Leu Glu Gln Met Thr
                165                 170                 175

Leu Pro Asp Asp Phe Asn Ser Gly Asn Thr Leu Gln Asn Arg Asp Lys
            180                 185                 190

Asn Arg Tyr Arg Asp Ile Leu Pro Tyr Asp Ser Thr Arg Val Pro Leu
        195                 200                 205

Gly Lys Asn Lys Asp Tyr Ile Asn Ala Ser Tyr Ile Arg Ile Val Asn
    210                 215                 220

His Glu Glu Glu Tyr Phe Tyr Ile Ala Thr Gln Gly Pro Leu Pro Glu
225                 230                 235                 240

Thr Ile Glu Asp Phe Trp Gln Met Val Leu Glu Asn Asn Cys Asn Val
                245                 250                 255

Ile Ala Met Ile Thr Arg Glu Ile Glu Cys Gly Val Ile Lys Cys Tyr
            260                 265                 270

Ser Tyr Trp Pro Ile Ser Leu Lys Glu Pro Leu Glu Phe Glu His Phe
        275                 280                 285

Ser Val Phe Leu Glu Thr Phe His Val Thr Gln Tyr Phe Thr Val Arg
    290                 295                 300

Val Phe Gln Ile Val Lys Lys Ser Thr Gly Lys Ser Gln Cys Val Lys
```

-continued

```
                305                 310                 315                 320

His Leu Gln Phe Thr Lys Trp Pro Asp His Gly Thr Pro Ala Ser Ala
                325                 330                 335

Asp Phe Phe Ile Lys Tyr Val Arg Tyr Val Arg Lys Ser His Ile Thr
                340                 345                 350

Gly Pro Leu Leu Val His Cys Ser Ala Gly Val Gly Arg Thr Gly Val
                355                 360                 365

Phe Ile Cys Val Asp Val Val Phe Ser Ala Ile Glu Lys Asn Tyr Ser
370                 375                 380

Phe Asp Ile Met Asn Ile Val Thr Gln Met Arg Lys Gln Arg Cys Gly
385                 390                 395                 400

Met Ile Gln Thr Lys Glu Gln Tyr Gln Phe Cys Tyr Glu Ile Val Leu
                405                 410                 415

Glu Val Leu Gln Asn Leu Leu Ala Leu Tyr
                420                 425
```

(2) INFORMATION FOR SEQ ID NO:6:

(i) SEQUENCE CHARACTERISTICS:
        (A) LENGTH:       463 amino acids
        (B) TYPE:         amino acid
        (C) STRANDEDNESS:  single
        (D) TOPOLOGY:     linear (ii) MOLECULE TYPE:     peptide (xi) SEQUENCE DESCRIPTION: SEQ ID NO:6:

```
Met Ser Ser Pro Arg Lys Val Arg Gly Lys Thr Gly Arg Asp Asn Asp
1               5                   10                  15

Glu Glu Glu Gly Asn Ser Gly Asn Leu Asn Leu Arg Asn Ser Leu Pro
                20                  25                  30

Ser Ser Ser Gln Lys Met Thr Pro Thr Lys Pro Val Gln Asn Lys Asn
            35                  40                  45

Leu Met Lys Tyr Glu Glu His Leu Asp Ile Leu Met Val Phe Leu Leu
    50                  55                  60

Ile Lys Thr Ile Trp Tyr Asn Val Phe Lys Leu Trp Lys Gly Lys Leu
65                  70                  75                  80

Ile Phe Gly Asn Lys Met Asn Ser Glu Asn Val Lys Pro Ser His His
                85                  90                  95

Leu Ser Phe Ser Asp Lys Tyr Glu Leu Val Tyr Pro Glu Pro Leu Glu
                100                 105                 110

Ser Asp Thr Asp Glu Thr Val Trp Asp Val Ser Asp Arg Ser Leu Arg
            115                 120                 125

Asn Arg Trp Asn Ser Met Asp Ser Glu Thr Ala Gly Pro Ser Lys Thr
    130                 135                 140

Val Ser Pro Val Leu Ser Gly Ser Ser Arg Leu Ser Lys Asp Thr Glu
145                 150                 155                 160

Thr Ser Val Ser Glu Lys Glu Leu Thr Gln Leu Ala Gln Ile Arg Pro
                165                 170                 175

Leu Ile Phe Asn Ser Ser Ala Arg Ser Ala Met Arg Asp Cys Leu Asn
                180                 185                 190

Thr Leu Gln Lys Lys Glu Glu Leu Asp Ile Ile Arg Glu Phe Leu Glu
            195                 200                 205

Leu Glu Gln Met Thr Leu Pro Asp Asp Phe Asn Ser Gly Asn Thr Leu
    210                 215                 220

Gln Asn Arg Asp Lys Asn Arg Tyr Arg Asp Ile Leu Pro Tyr Asp Ser
```

-continued

```
                225                 230                 235                 240
Thr Arg Val Pro Leu Gly Lys Asn Lys Asp Tyr Ile Asn Ala Ser Tyr
                    245                 250                 255

Ile Arg Ile Val Asn His Glu Glu Tyr Phe Tyr Ile Ala Thr Gln
                260                 265                 270

Gly Pro Leu Pro Glu Thr Ile Glu Asp Phe Trp Gln Met Val Leu Glu
                275                 280                 285

Asn Asn Cys Asn Val Ile Ala Met Ile Thr Arg Glu Ile Glu Cys Gly
290                 295                 300

Val Ile Lys Cys Tyr Ser Tyr Trp Pro Ile Ser Leu Lys Glu Pro Leu
305                 310                 315                 320

Glu Phe Glu His Phe Ser Val Phe Leu Glu Thr Phe His Val Thr Gln
                325                 330                 335

Tyr Phe Thr Val Arg Val Phe Gln Ile Val Lys Lys Ser Thr Gly Lys
                340                 345                 350

Ser Gln Cys Val Lys His Leu Gln Phe Thr Lys Trp Pro Asp His Gly
            355                 360                 365

Thr Pro Ala Ser Ala Asp Phe Phe Ile Lys Tyr Val Arg Tyr Val Arg
            370                 375                 380

Lys Ser His Ile Thr Gly Pro Leu Leu Val His Cys Ser Ala Gly Val
385                 390                 395                 400

Gly Arg Thr Gly Val Phe Ile Cys Val Asp Val Val Phe Ser Ala Ile
                    405                 410                 415

Glu Lys Asn Tyr Ser Phe Asp Ile Met Asn Ile Val Thr Gln Met Arg
                420                 425                 430

Lys Gln Arg Cys Gly Met Ile Gln Thr Lys Glu Gln Tyr Gln Phe Cys
            435                 440                 445

Tyr Glu Ile Val Leu Glu Val Leu Gln Asn Leu Leu Ala Leu Tyr
            450                 455                 460
```

(2) INFORMATION FOR SEQ ID NO:7:

(i) SEQUENCE CHARACTERISTICS:
        (A) LENGTH:       405 amino acids
        (B) TYPE:         amino acid
        (C) STRANDEDNESS:  single
        (D) TOPOLOGY:     linear (ii) MOLECULE TYPE:      peptide (xi) SEQUENCE DESCRIPTION: SEQ ID NO:7:

```
Met Ser Ser Pro Arg Lys Val Arg Gly Lys Thr Gly Arg Asp Asn Asp
1               5                   10                  15

Glu Glu Glu Gly Asn Ser Gly Asn Leu Asn Leu Arg Asn Ser Leu Pro
                20                  25                  30

Ser Ser Ser Gln Lys Met Thr Pro Thr Lys Pro Ile Phe Gly Asn Lys
            35                  40                  45

Met Asn Ser Glu Asn Val Lys Pro Ser His His Leu Ser Phe Ser Asp
    50                  55                  60

Lys Tyr Glu Leu Val Tyr Pro Glu Pro Leu Glu Ser Asp Thr Asp Glu
65                  70                  75                  80

Thr Val Trp Asp Val Ser Asp Arg Ser Leu Arg Asn Arg Trp Asn Ser
                85                  90                  95

Met Asp Ser Glu Thr Ala Gly Pro Ser Lys Thr Val Ser Pro Val Leu
                100                 105                 110

Ser Gly Ser Ser Arg Leu Ser Lys Asp Thr Glu Thr Ser Val Ser Glu
```

-continued

```
            115                 120                 125
Lys Glu Leu Thr Gln Leu Ala Gln Ile Arg Pro Leu Ile Phe Asn Ser
    130                 135                 140

Ser Ala Arg Ser Ala Met Arg Asp Cys Leu Asn Thr Leu Gln Lys Lys
145                 150                 155                 160

Glu Glu Leu Asp Ile Ile Arg Glu Phe Leu Glu Leu Glu Gln Met Thr
                165                 170                 175

Leu Pro Asp Asp Phe Asn Ser Gly Asn Thr Leu Gln Asn Arg Asp Lys
            180                 185                 190

Asn Arg Tyr Arg Asp Ile Leu Pro Tyr Asp Ser Thr Arg Val Pro Leu
        195                 200                 205

Gly Lys Asn Lys Asp Tyr Ile Asn Ala Ser Tyr Ile Arg Ile Val Asn
    210                 215                 220

His Glu Glu Glu Tyr Phe Tyr Ile Ala Thr Gln Gly Pro Leu Pro Glu
225                 230                 235                 240

Thr Ile Glu Asp Phe Trp Gln Met Val Leu Glu Asn Asn Cys Asn Val
                245                 250                 255

Ile Ala Met Ile Thr Arg Glu Ile Glu Cys Gly Val Ile Lys Cys Tyr
            260                 265                 270

Ser Tyr Trp Pro Ile Ser Leu Lys Glu Pro Leu Glu Phe Glu His Phe
        275                 280                 285

Ser Val Phe Leu Glu Thr Phe His Val Thr Gln Tyr Phe Thr Val Arg
    290                 295                 300

Val Phe Gln Ile Val Lys Lys Ser Thr Gly Lys Ser Gln Cys Val Lys
305                 310                 315                 320

His Leu Gln Phe Thr Lys Trp Pro Asp His Gly Thr Pro Ala Ser Ala
                325                 330                 335

Asp Phe Phe Ile Lys Tyr Val Arg Tyr Val Arg Lys Ser His Ile Thr
            340                 345                 350

Gly Pro Leu Leu Val His Cys Ser Ala Gly Val Gly Arg Thr Gly Val
        355                 360                 365

Phe Ile Cys Val Asp Val Val Phe Ser Ala Ile Glu Lys Asn Tyr Ser
    370                 375                 380

Phe Asp Ile Met Asn Ile Val Thr Gln Met Arg Lys Gln Arg Cys Gly
385                 390                 395                 400

Met Ile Gln Thr Lys
            405

(2) INFORMATION FOR SEQ ID NO:8:

(i) SEQUENCE CHARACTERISTICS:
        (A) LENGTH:        122 amino acids
        (B) TYPE:          amino acid
        (C) STRANDEDNESS:  single
        (D) TOPOLOGY:      linear (ii) MOLECULE TYPE:        peptide (xi) SEQUENCE DESCRIPTION: SEQ ID NO:8:

Asp Phe Trp Gly Met Met Trp Glu Asn Asn Cys Asn Val Ile Ala Met
1               5                   10                  15

Ile Thr Arg Glu Ile Glu Gly Gly Val Ile Lys Cys Cys Ser Tyr Trp
                20                  25                  30

Pro Val Ser Leu Lys Glu Pro Leu Glu Phe Lys His Phe His Val Leu
            35                  40                  45

Leu Glu Asn Phe Gln Ile Thr Gln Tyr Phe Val Ile Arg Ile Phe Gln
```

```
            50                  55                  60
Ile Val Lys Lys Ser Thr Gly Lys Ser His Ser Val Lys His Leu Gln
 65                  70                  75                  80

Phe Ile Lys Trp Pro Asp His Gly Thr Pro Ala Ser Val Asp Phe Phe
                 85                  90                  95

Ile Lys Tyr Val Arg Tyr Val Arg Lys Ser His Ile Thr Gly Pro Leu
            100                 105                 110

Leu Val His Cys Thr Ala Gly Val Gly Arg
            115                 120
```

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION: The letter "Y" stands for C or T.
           The letter "V" stands for A, C or G.
           The letter "R" stands for A or G.
           The letter "N" stands for A, C, G or T.

(xi) SEQUENCE DESCRIPTION: SEQ ID NO:9:

```
GAYTTYTGGV RNATGRTNTG GGA                                       23
```

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION: The letter "S" stands for C or G.
           The letter "Y" stands for C or T.
           The letter "N" stands for A, C, G or T.
           The letter "W" stands for A or T.
           The letter "R" stands for A or G.

(xi) SEQUENCE DESCRIPTION: SEQ ID NO:10:

```
CGGCCSAYNC CNGCNSWRCA RTG                                       23
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ix) FEATURE:
        (D) OTHER INFORMATION: "Xaa" in positions 4 and 6 stand for an unspecified amino acid.
           "Xaa" in position 8 stands for either Glu or Asp.

(ii) MOLECULE TYPE: peptide (xi) SEQUENCE DESCRIPTION: SEQ ID NO:11:

```
Asp Phe Trp Xaa Met Xaa Trp Xaa
 1               5
```

```
(2) INFORMATION FOR SEQ ID NO:12:

(i) SEQUENCE CHARACTERISTICS:
        (A) LENGTH:         7 amino acids
        (B) TYPE:           amino acid
        (C) STRANDEDNESS:   single
        (D) TOPOLOGY:       linear (ii) MOLECULE TYPE:     peptide (ix) FEATURE:
        (D) OTHER INFORMATION:  "Xaa" in positions 3 and 6 stand
            for an unspecified amino acid.

(xi) SEQUENCE DESCRIPTION: SEQ ID NO:12:

His Cys Xaa Ala Gly Xaa Gly
 1               5

(2) INFORMATION FOR SEQ ID NO:13:

(i) SEQUENCE CHARACTERISTICS:
        (A) LENGTH:         34 base pairs
        (B) TYPE:           nucleic acid
        (C) STRANDEDNESS:   single
        (D) TOPOLOGY:       linear (xi) SEQUENCE DESCRIPTION: SEQ ID NO:13:

CACCGTTCGA GTATTTCAGA TTGTGAAGAA GTCC                          34

(2) INFORMATION FOR SEQ ID NO:14:

(i) SEQUENCE CHARACTERISTICS:
        (A) LENGTH:         34 base pairs
        (B) TYPE:           nucleic acid
        (C) STRANDEDNESS:   single
        (D) TOPOLOGY:       linear (xi) SEQUENCE DESCRIPTION: SEQ ID NO:14:

GGACTTCTTC ACAATCTGAA ATACTCGAAC GGTG                          34

(2) INFORMATION FOR SEQ ID NO:15:

(i) SEQUENCE CHARACTERISTICS:
        (A) LENGTH:         33 base pairs
        (B) TYPE:           nucleic acid
        (C) STRANDEDNESS:   single
        (D) TOPOLOGY:       linear (xi) SEQUENCE DESCRIPTION: SEQ ID NO:15:

CCGTTATGTG AGGAAGAGCC ACATTACAGG ACC                           33

(2) INFORMATION FOR SEQ ID NO:16:

(i) SEQUENCE CHARACTERISTICS:
        (A) LENGTH:         33 base pairs
        (B) TYPE:           nucleic acid
        (C) STRANDEDNESS:   single
        (D) TOPOLOGY:       linear (xi) SEQUENCE DESCRIPTION: SEQ ID NO:16:

GGTCCTGTAA TGTGGCTCTT CCTCACATAA CGG                           33

(2) INFORMATION FOR SEQ ID NO:17:

(i) SEQUENCE CHARACTERISTICS:
        (A) LENGTH:         34 base pairs
        (B) TYPE:           nucleic acid
        (C) STRANDEDNESS:   single
        (D) TOPOLOGY:       linear
```

(xi) SEQUENCE DESCRIPTION: SEQ ID NO:17:

CACCGTTCGA GTATTTCAGA TTGTGAAGAA GTCC                      34

(2) INFORMATION FOR SEQ ID NO:18:

(i) SEQUENCE CHARACTERISTICS:
                (A) LENGTH:         33 base pairs
                (B) TYPE:           nucleic acid
                (C) STRANDEDNESS:   single
                (D) TOPOLOGY:       linear (xi) SEQUENCE DESCRIPTION: SEQ ID NO:18:

GGTCCTGTAA TGTGGCTCTT CCTCACATAA CGG                       33

(2) INFORMATION FOR SEQ ID NO:19:

(i) SEQUENCE CHARACTERISTICS:
                (A) LENGTH:         10 amino acids
                (B) TYPE:           amino acid
                (C) STRANDEDNESS:   single
                (D) TOPOLOGY:       linear (ii) MOLECULE TYPE:         peptide (xi) SEQUENCE DESCRIPTION: SEQ ID NO:19:

Tyr Pro Tyr Asp Val Pro Asp Tyr Ala Ser
1               5                   10

(2) INFORMATION FOR SEQ ID NO:20:

(i) SEQUENCE CHARACTERISTICS:
                (A) LENGTH:         5 amino acids
                (B) TYPE:           amino acid
                (C) STRANDEDNESS:   single
                (D) TOPOLOGY:       linear (ii) MOLECULE TYPE:         peptide (xi) SEQUENCE DESCRIPTION: SEQ ID NO:20:

His Cys Ser Ala Gly
1               5

(2) INFORMATION FOR SEQ ID NO:21:

(i) SEQUENCE CHARACTERISTICS:
                (A) LENGTH:         29 amino acids
                (B) TYPE:           amino acid
                (C) STRANDEDNESS:   single
                (D) TOPOLOGY:       linear (ii) MOLECULE TYPE:         peptide (xi) SEQUENCE DESCRIPTION: SEQ ID NO:21:

Met Ser Ser Pro Arg Lys Val Arg Gly Lys Thr Gly Arg Asp Asn Asp
1               5                   10                  15

Glu Glu Glu Gly Asn Ser Gly Asn Leu Asn Leu Arg Asn
            20                  25

(2) INFORMATION FOR SEQ ID NO:22:

(i) SEQUENCE CHARACTERISTICS:
                (A) LENGTH:         29 amino acids
                (B) TYPE:           amino acid
                (C) STRANDEDNESS:   single
                (D) TOPOLOGY:       linear (ii) MOLECULE TYPE:         peptide (xi) SEQUENCE DESCRIPTION: SEQ ID NO:22:

Ser Pro Val Leu Ser Gly Ser Ser Arg Leu Ser Lys Asp Thr Glu Thr
1               5                   10                  15

Ser Val Ser Glu Lys Glu Leu Thr Gln Leu Ala Gln Ile
            20                  25

(2) INFORMATION FOR SEQ ID NO:23:

(i) SEQUENCE CHARACTERISTICS:
        (A) LENGTH:         29 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO:23:

Trp Asp Val Ser Asp Arg Ser Leu Arg Asn Arg Trp Asn Ser Met Asp
1               5                   10                  15

Ser Glu Thr Ala Gly Pro Ser Lys Thr Val Ser Pro Val
            20                  25